(12) United States Patent
Murthy

(10) Patent No.: US 7,402,697 B2
(45) Date of Patent: Jul. 22, 2008

(54) ANTIBACTERIAL AGENTS

(75) Inventor: Yerramilli V. S. N. Murthy, Apex, NC (US)

(73) Assignee: Idexx Laboratories Inc., Westbrook, ME (US)

( * ) Notice: Subject to any disclaimer, the term of this patent is extended or adjusted under 35 U.S.C. 154(b) by 18 days.

(21) Appl. No.: 11/208,889

(22) Filed: Aug. 23, 2005

(65) Prior Publication Data

US 2006/0047138 A1 Mar. 2, 2006

Related U.S. Application Data

(60) Provisional application No. 60/606,513, filed on Sep. 2, 2004.

(51) Int. Cl.
*C07C 233/03* (2006.01)
*A61N 37/18* (2006.01)

(52) U.S. Cl. .................. 564/202; 564/211; 514/625; 514/628; 514/629

(58) Field of Classification Search ............... 514/625, 514/628, 629; 564/202, 211
See application file for complete search history.

(56) References Cited

U.S. PATENT DOCUMENTS

| 4,235,892 | A | | 11/1980 | Nagabhushan | |
|---|---|---|---|---|---|
| 4,743,700 | A | * | 5/1988 | Jommi et al. | 548/216 |
| 5,336,664 | A | * | 8/1994 | Camaggi et al. | 504/261 |
| 5,476,854 | A | | 12/1995 | Young | |
| 5,556,829 | A | | 9/1996 | Camaggi et al. | |
| 5,883,115 | A | | 3/1999 | Santus et al. | |
| 2003/0216447 | A1 | | 11/2003 | Kohan et al. | |
| 2003/0220302 | A1 | | 11/2003 | Kohan et al. | |

FOREIGN PATENT DOCUMENTS

WO    WO 03/077828 A3    9/2003

OTHER PUBLICATIONS

F.E. Hahn, *Antibiotics*, Ed.Gottlieb and Shaw, Springer-Verlag, New York, (1967) p. 308.
F.E. Hahn, et al., *Antibiotics and Chemotherapy*, 6, No. 9, 531 (1956).
L. Cima and A. Ilecto, II Farmaco, Ed. Sc. 12, No. 6, 535 (1957).
S. Mitsuhasi et al., *Jap. J. Microbiol.* 13, No. 2, 177-80 (1969).
M. Kono et al., *Jap. J. Microbiology* 15(3), 219-27 (1971).
Maier et al.: *Separation of enantiomers: needs, challenges, perspectives*, Journal of Chromatography, 2001, vol. 906, pp. 3-33.

* cited by examiner

*Primary Examiner*—Shailendra Kumar
(74) *Attorney, Agent, or Firm*—Townsend and Townsend and Crew LLP.

(57) ABSTRACT

D-(threo)-1-aryl-2-disubstitutedacylamido-3-fluoro-1-propanol compounds compounds and analogues thereof ("Fenicol Compounds"), compositions comprising an effective amount of a Fenicol Compound, and methods for treating or preventing a bacterial infection in an animal comprising administering to an animal in need thereof an effective amount of a Fenicol Compound are disclosed.

25 Claims, 3 Drawing Sheets

ANTIBACTERIAL AGENTS

CROSS-REFERENCE TO RELATED APPLICATIONS

Figure 1:
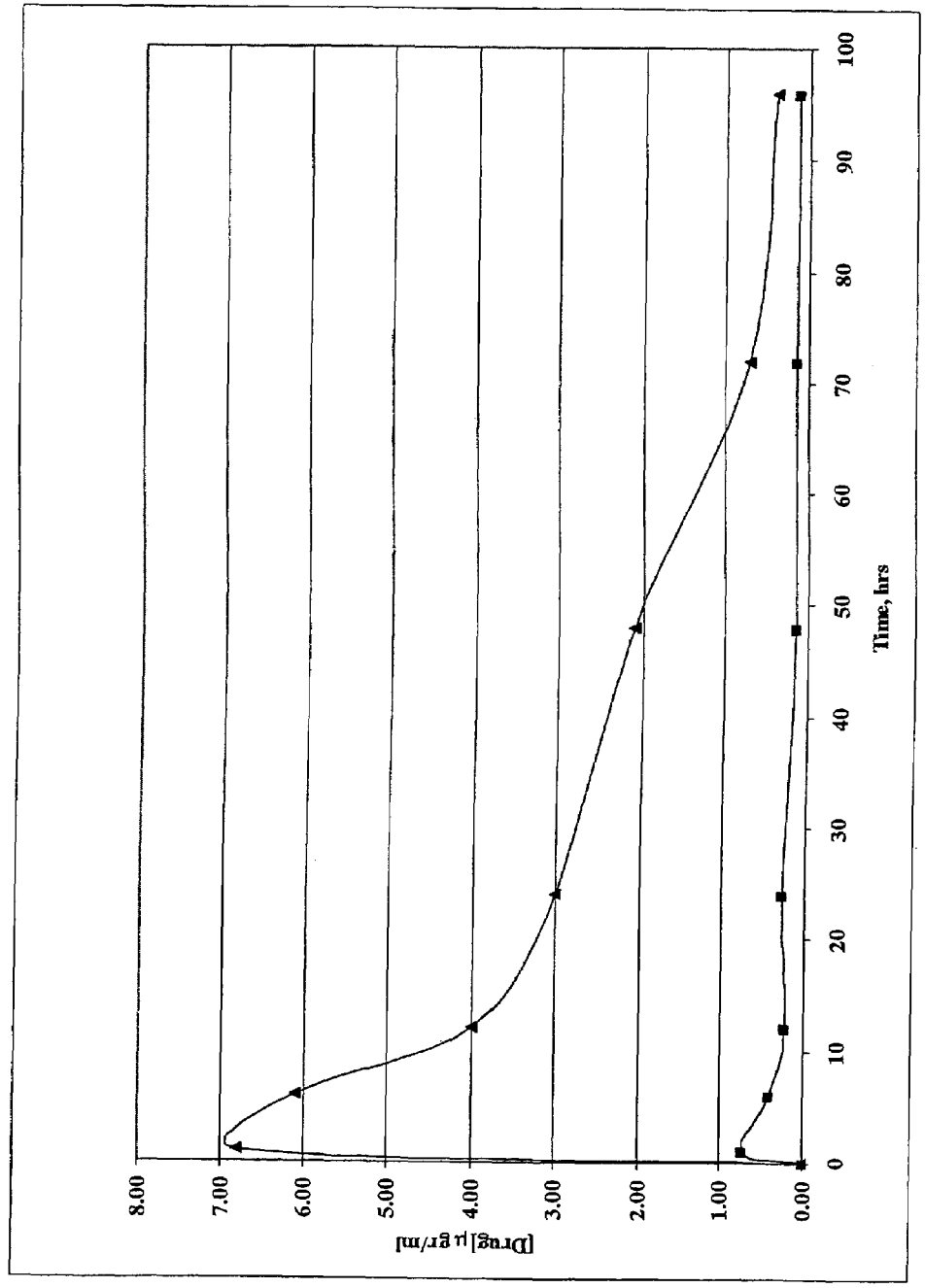

This application claims priority under 35 USC § 120 of provisional application No. 60/606,513 filed 02 Sep. 2004, the content of which is incorporated herein by reference.

1. FIELD OF THE INVENTION

The present invention is related to D-(threo)-1-aryl-2-disubstitutedacylamido-3-fluoro-1-propanol compounds compounds and analogues thereof ("Fenicol Compounds") that are useful as broad spectrum antibiotics, pharmaceutical compositions comprising the Fenicol Compounds, and methods of treating or preventing bacterial infections in an animal comprising administering to an animal in need thereof an effective amount of a Fenicol Compound. The invention further relates to methods for preparing the Fenicol Compounds.

2. BACKGROUND OF THE INVENTION

Bacterial infections, especially bacterial infections of the respiratory tract, are a major problem for production animals such as cattle, pigs, sheep, and other livestock. Bacterial infections are also a common problem with companion animals such as cats, dogs, and horses. Bacterial infections are typically treated using antibiotics.

A class of broad spectrum antibiotics classified as D-(threo)-1-p-substituted phenyl-2-halogenoacetylamido-1,3-propanediols are known in the art. This class of antibiotics includes chloramphenicol (D-(threo)-1-p-nitrophenyl-2-dichloroacetamido-1,3-propanediol), thiamphenicol (D-(threo)-1-p-methylsulfonylphenyl-2-dichloroacetamido-1,3-propanediol), fluorthiamphenicol (D-(threo)-1-p-methylsulfonylphenyl-2-difluoroacetamido-1,3-propanediol) and tevenel (D-(threo)-1-p-aminosulfonylphenyl-2-dichloroacetamido-1,3-propanediol) (See, U.S. Pat. No. 4,235,892 to Nagabhushan). Replacing the primary hydroxyl group at C-3 of chloramphenicol by chlorine or bromine, however, destroys the biological activity thereof (F. E. Hahn, *Antibiotics*, Ed. Gottlieb and Shaw, Springer-Verlag, New York, (1967), p. 308; F. E. Hahn et al, *Antibiotics and Chemotherapy*, 6, No. 9, 531 (1956); L. Cima and A. Ilecto, Il Farmaco, Ed. Sc. 12, No. 6, 535 (1957); S. Mitsuhasi et al, *Jap. J. Microbiol.* 13, No. 2, 177-80 (1969); M. Kono et al, *Jap. J. Microbiology* 15 (3), 219-27 (1971); and U.S. Pat. No. 4,235,892 to Nagabhushan).

U.S. Pat. No. 4,235,892 to Nagabhushan discloses D-(threo)-1-aryl-2-acylamido-3-fluoro-1-propanol compounds that are allegedly useful as antibiotics. Florfenicol, [(R-(R*, S*)]-2,2-dichloro-N-[1-fluoromethyl)-2-hydroxy-2-[4-(methylsulfonyl)phenyl] ethyl]acetamide or D-threo-2, 2-dichloro-N-[1-(fluoromethyl)-2-hydroxy-2-[4-methylsulfonyl) phenyl]ethyl]-acetamide), commercially available from Schering-Plough Animal Health, New Jersey as NUFLOR®, is an example of an antibiotic in this class of compounds.

United States published patent application no. U.S. 2003/0216447 to Kohan et al. and United States published patent application no. U.S. 2003/0220302 also to Kohan et al. each disclose compositions comprising flunixin and a florfenicol or florfenicol-like compound that are allegedly useful for treating microbial infections in animals.

International publication WO 03/077828 discloses fluorfenicol-type antibiotics that allegedly exhibit antimicrobial activity.

U.S. Pat. No. 5,556,829 to Camaggi et al. discloses N-alkyl amides substituted on the alkyl group that are allegedly useful as herbicides.

U.S. Pat. No. 5,883,115 to Santus et al. discloses the transdermal delivery of the eutmer of a chiral drug when the eutomer has greater clearance and pharmacodynamic activity than a racemic mixture of the chiral drug.

Many of the known antibiotics, however, have side effects. For example, chloramphenicol is known to cause anemia. Furthermore, the known antibiotics can be ineffective in some animals, typically because they are cleared too rapidly. Additionally, some of the antibiotics are toxic to some animals. Accordingly, there is a need in the art for improved antibiotics and, in particular, new antibiotics that fall within the same general class as the D-(threo)-1-p-substituted phenyl-2-halogenoacetylamido-1,3-propanediols and the D-(threo)-1-aryl-2-acylamido-3-fluoro-1-propanol compounds.

Citation of any reference in Section 2 of this application is not to be construed that such reference is prior art to the present application.

3. SUMMARY OF THE INVENTION

The invention is directed to compounds of formula (I):

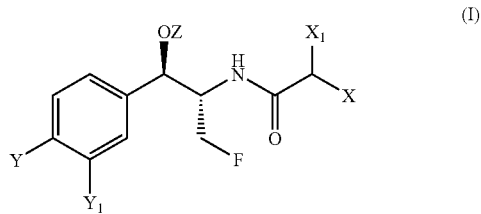

(I)

or a pharmaceutically acceptable salt thereof, wherein
X is —CH$_3$ and X$_1$ is —CH$_3$, —CF$_3$, or —OH or
X is —CF$_3$ and X$_1$ is —CF$_3$; -halo, or —OH;
Z is hydrogen or an acyl group of formula —C(O)—R$_2$, wherein R$_2$ is a C$_1$ to C$_{18}$ hydrocarbon group that may optionally be substituted with a —NH$_2$ or —COOH;
Y and Y$^1$ is —H; —NO$_2$; —SOR$_1$; —SR$_1$; —SONH$_2$; —SO$_2$NH$_2$; —SONHR$_1$; —SO$_2$NHR$_1$; —COR$_1$; —OR$_1$; —R$_1$; —CN, -halo; -phenyl; or -phenyl substituted with -halo, —NO$_2$, —SO$_2$CH$_3$, —R$_1$, or —OR$_1$;
—R$_1$ is a C$_1$ to C$_3$ hydrocarbon group; and
halo is —Cl, —Br, —I, or —F.

The invention further relates to compounds of formula (Ia):

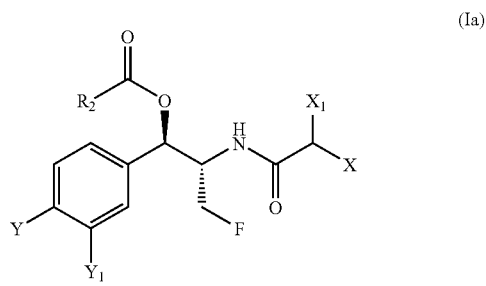

(Ia)

and pharmaceutically acceptable salts thereof, wherein
X is —$CH_3$ and $X_1$ is —$CH_3$, —$CF_3$, or —OH or
X is —$CF_3$ and $X_1$ is —$CF_3$; -halo, or —OH;
$R_2$ is a $C_1$ to $C_{18}$ hydrocarbon group that may optionally be substituted with a —$NH_2$ or —COOH;
Y and $Y^1$ is —H; —$NO_2$; —$SO_2R_1$; —$SOR_1$; —$SR_1$; —$SONH_2$; —$SO_2NH_2$; —$SONHR_1$; —$SO_2NHR_1$; —$COR_2$; —$OR_1$; —$R_1$; —CN, -halo; -phenyl; or -phenyl substituted with -halo, —$NO_2$, —$SO_2CH_3$, —$R_1$, or —$OR_1$;
$R_1$ is a $C_1$ to $C_3$ hydrocarbon group; and
halo is —Cl, —Br, —I, or —F.

The invention is further directed to compounds of formula (II):

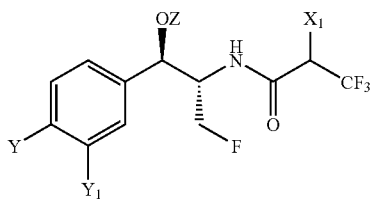

or a pharmaceutically acceptable salt thereof, wherein
$X_1$ is —$CH_3$, —$CF_3$; -halo, or —OH;
Z is hydrogen or an acyl group of formula —C(O)—$R_2$, wherein $R_2$ is a $C_1$ to $C_{18}$ hydrocarbon group that may optionally be substituted with a —$NH_2$ or —COOH;
Y and $Y^1$ is —H; —$NO_2$; —$SO_2R_1$; —$SOR_1$; —$SR_1$; —$SONH_2$; —$SO_2NH_2$; —$SONHR_1$; —$SO_2NHR_1$; —$COR_1$; —$OR_1$; —$R_1$; —CN, -halo; -phenyl; or -phenyl substituted with -halo, —$NO_2$, —$SO_2CH_3$, —$R_1$, or —$OR_1$;
$R_1$ is a $C_1$ to $C_3$ hydrocarbon group; and
halo is —Cl, —Br, —I, or —F.

The invention is further directed to compounds of formula (III):

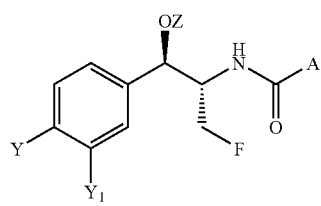

or a pharmaceutically acceptable salt thereof,
wherein
A is (R) —$CH(CH_3)(CF_3)$ substantially free of (S) —$CH(CH_3)(CF_3)$, (R) —$CH(CH_3)$(halo) substantially free of (S) —$CH(CH_3)$(halo), (R) —$CH(CF_3)$(halo) substantially free of (S) —$CH(CF_3)$(halo), (R)-$CH(CF_3)$(OH) substantially free of (S) —$CH(CF_3)$(OH), (S) —$CH(CH_3)(CF_3)$ substantially free of (R) —$CH(CH_3)(CF_3)$, (S) —$CH(CH_3)$(halo) substantially free of (R) —$CH(CH_3)$(halo), (S) —$CH(CF_3)$(halo) substantially free of (R) —$CH(CF_3)$(halo), or (S)$CH(CF_3)$(OH) substantially free of (R) —$CH(CF_3)$(OH);

Z is hydrogen or an acyl group of formula —C(O)—$R_2$, wherein $R_2$ is a $C_1$ to $C_{18}$ hydrocarbon group that may optionally be substituted with a —$NH_2$ or —COOH;
Y and $Y^1$ is —H; —$NO_2$; —$SO_2R_1$; —$SOR_1$; —$SR_1$; —$SONH_2$; —$SO_2NH_2$; —$SONHR_1$; —$SO_2NHR_1$; —$COR_2$; —$OR_1$; —$R_1$; —CN, -halogen; -phenyl; or -phenyl substituted with -halogen, —$NO_2$, —$SO_2CH_3$, —$R_1$, or —$OR_1$;
halo is —Cl, —Br, —I, or —F; and
$R_1$ is a $C_1$ to $C_3$ hydrocarbon group.

A compound of formula (I), (Ia), (II), or (III) or a pharmaceutically acceptable salt thereof is useful for treating or preventing bacterial infections in animals.

The invention further relates to a method for treating or preventing a bacterial infection in an animal comprising administering to an animal in need thereof a compound of formula (IV):

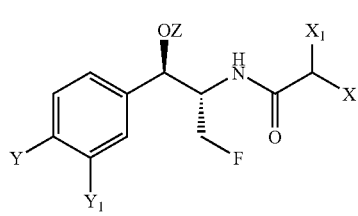

or a pharmaceutically acceptable salt thereof, wherein
X is —$CH_3$ and $X_1$ is —$CH_3$, —$CF_3$, or —OH or
X is —$CF_3$ and $X_1$ is —$CF_3$, -halo, or —OH;
Z is hydrogen or an acyl group of formula —C(O)—$R_2$, wherein $R_2$ is a $C_1$ to $C_{18}$ hydrocarbon group that may optionally be substituted with a —$NH_2$ or —COOH;
Y and $Y^1$ is —H; —$NO_2$; —$SO_2R_1$; —$SOR_1$; —$SR_1$; —$SONH_2$; —$SO_2N$—$H_2$; —$SONHR_1$; —$SO_2NHR_1$; —$COR_2$; —$OR_1$; —$R_1$; —CN, -halo; -phenyl; or -phenyl substituted with -halo, —$NO_2$, —$SO_2CH_3$, —$R_1$, or —$OR_1$;
$R_1$ is a $C_1$ to $C_3$ hydrocarbon group; and
halo is —Cl, —Br, —I, or —F.

Accordingly, the invention relates to a method of treating or preventing a bacterial infection in an animal comprising administering to an animal in need thereof a compound of formula (I), (Ia), (II), (III), or (IV) or a pharmaceutically acceptable salt thereof (a "Fenicol Compound").

The invention further relates to a method for treating a bacterial infection in an animal comprising administering to the animal in need thereof an effective amount of a Fenicol Compound.

The invention further relates to a method for preventing a bacterial infection in an animal comprising administering to the animal in need thereof an effective amount of a Fenicol Compound.

The invention further relates to compositions comprising an effective amount of a Fenicol Compound and a pharmaceutically acceptable excipient. The compositions are useful for treating or preventing bacterial infections in animals.

The invention further relates to a method for preparing a composition comprising the step of admixing a Fenicol Compound and a pharmaceutically acceptable carrier or excipient.

The invention further relates to a kit comprising a container containing an effective amount of a Fenicol Compound.

The present invention can be understood more fully by reference to the following detailed description and illustrative examples, which are intended to exemplify non-limiting embodiments of the invention.

4. BRIEF DESCRIPTION OF THE DRAWINGS

FIG. 1 is a plot of the serum concentration of NUFLOR® and the serum concentration of an illustrative Fenicol Compound (Fenicol Compound A1) as a function of time following subcutaneous administration of Nuflor and Fenicol Compound A1 to dogs at a dose of 40 mg/kg. NUFLOR® was commercially available from Schering-Plough Animal Health, New Jersey. Fenicol Compound A1 was formulated as a solution containing 3 g of Fenicol Compound A1, 9 g N-methylpyrrolidone, 2.25 g propylene glycol, QS to 20 mL with polyethylene glycol. ▲ represents data for Fenicol Compound A1 and ■ represents data for NUFLOR®.

Figure 2:
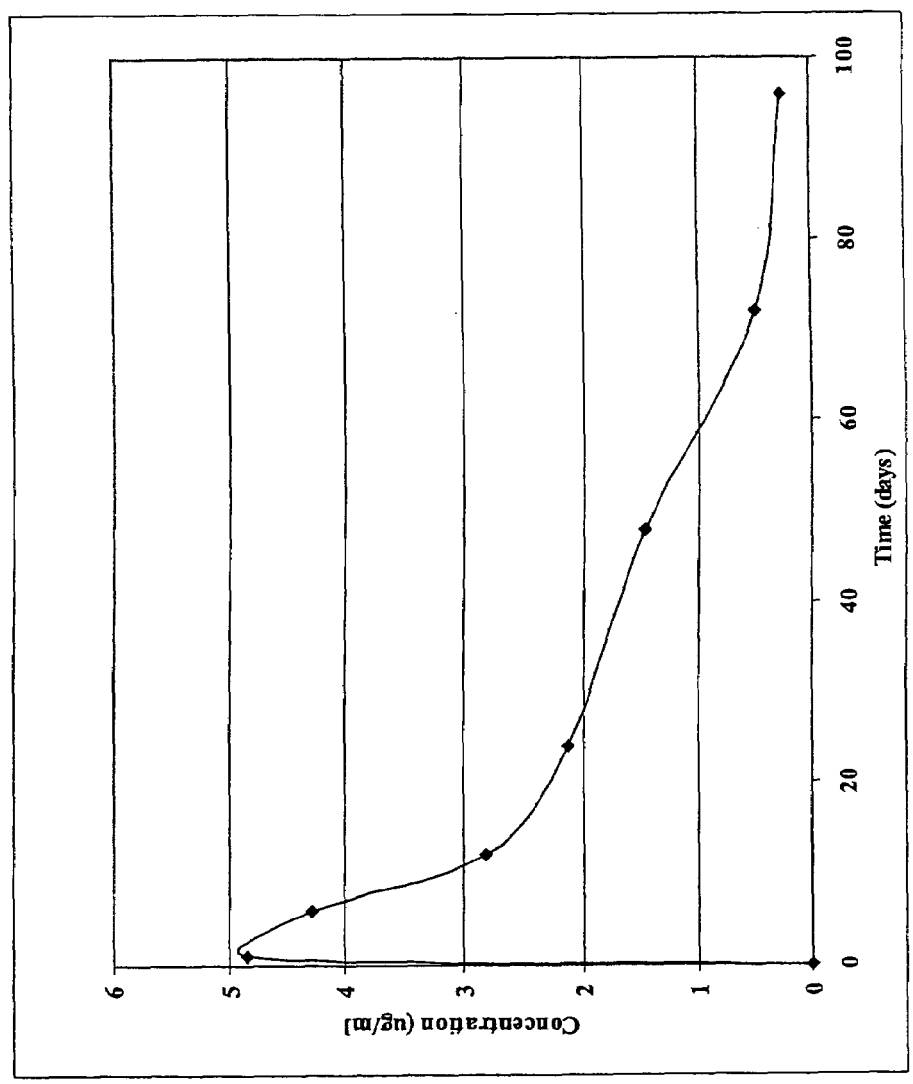

FIG. 2 is a plot of the serum concentration of an illustrative Fenicol Compound (Fenicol Compound A2) as a function of time following subcutaneous administration of Nuflor and Fenicol Compound A2 to dogs at a dose of 40 mg/kg. NUFLOR® was commercially available from Schering-Plough Animal Health, New Jersey. Fenicol Compound A2 was formulated as a solution containing 925 mg of Fenicol Compound A2, 2 mL N-methylpyrrolidone, 0.5 mL propylene glycol, QS to 5 mL with polyethylene glycol.

Figure 3:
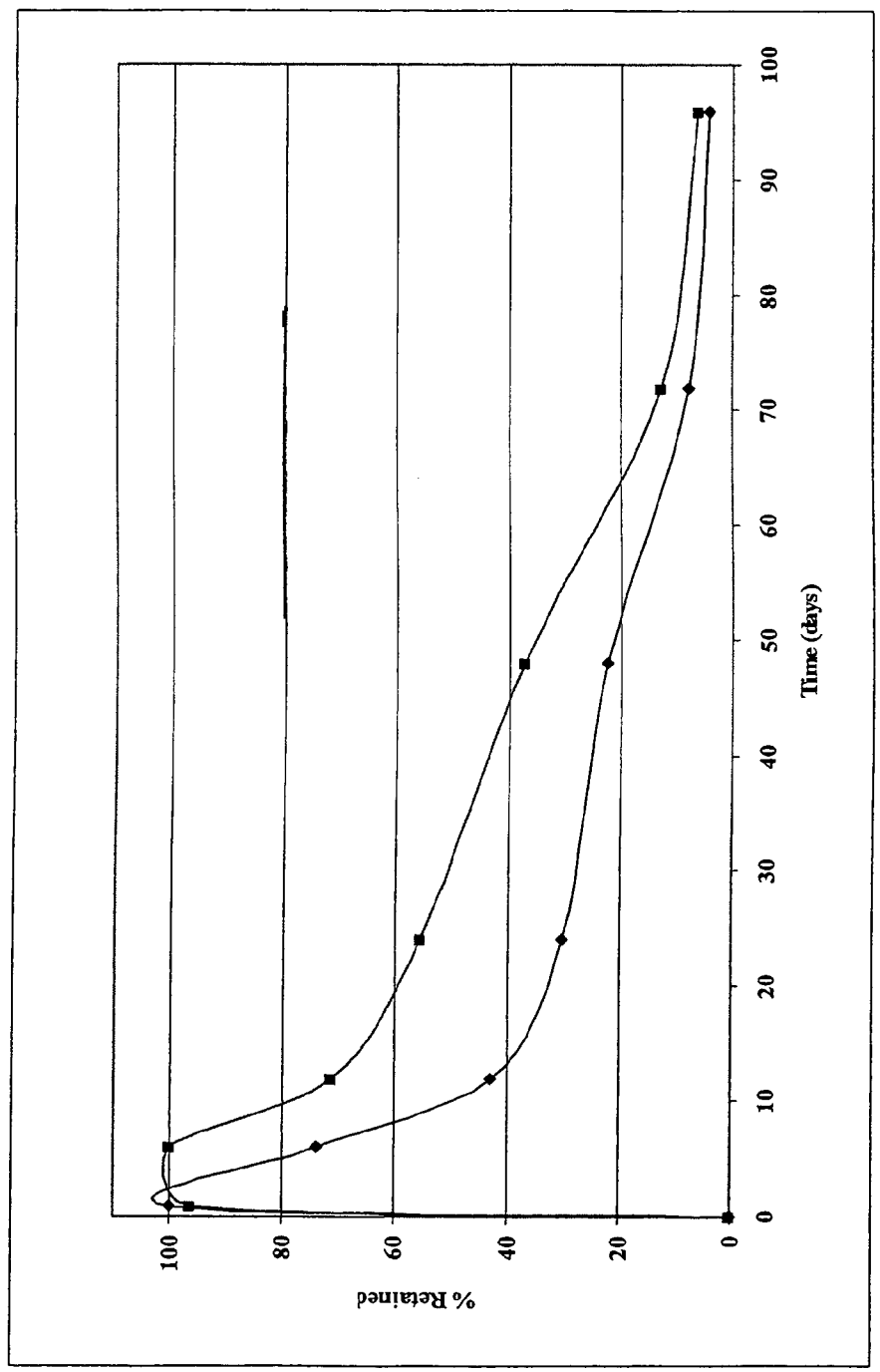

FIG. 3 is a plot of the serum concentration Fenicol Compound A2 wherin the acylamido group is in the (R) stereochemical configuration and the serum concentration of Fenicol Compound A2 wherein the acylamido group is in the the (S) stereochemical configuration as a function of time following subcutaneous administration to dogs of Fenicol Compound A2 wherein the acylamido group is present as an equimolar mixture of the (R) stereochemical configuration and the (S) stereochemical configuration at a dose of 40 mg/kg. Fenicol Compound A2 wherein the acylamido group is present as an equimolar mixture of the (R) stereochemical configuration and the (S) stereochemical configuration was administered as a solution containing 925 mg of Fenicol Compound A2 wherein the acylamido group is present as an equimolar mixture of the (R) stereochemical configuration and the (S) stereochemical configuration, 2 mL N-methylpyrrolidone, 0.5 mL propylene glycol, QS to 5 mL with polyethylene glycol.

5. DETAILED DESCRIPTION OF THE INVENTION

5.1 Fenicol Compounds of Formula (I)

As stated above, the present invention encompasses Fenicol Compounds of formula (I):

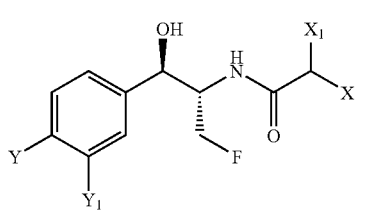

(I)

and pharmaceutically acceptable salts thereof, wherein
X is —CH$_3$ and X$_1$ is —CH$_3$, —CF$_3$, or —OH or
X is —CF$_3$ and X$_1$ is —CF$_3$, -halo, or —OH;
Y and Y$^1$ is —H; —NO$_2$; —SOR$_1$; —SR$_1$; —SONH$_2$; —SO$_2$NH$_2$; —SONHR$_1$; —SO$_2$NHR$_1$; —COR$_2$; —OR$_1$; —R$_1$; —CN; -halo; -phenyl; or -phenyl substituted with -halo, —NO$_2$, —SO$_2$CH$_3$, —R$_1$, or —OR$_1$;
R$_1$ is a C$_1$ to C$_3$ hydrocarbon group; and
halo is —Cl, —Br, —I, or —F.

In one embodiment, Y$_1$ is hydrogen.
In one embodiment, Y$_1$ is hydrogen and Y is hydrogen.
In one embodiment, Y$_1$ is hydrogen and Y is —NO$_2$.
In one embodiment, Y$_1$ is hydrogen and Y is —SOR$_1$.
In one embodiment, Y$_1$ is hydrogen and Y is —SR$_1$.
In one embodiment, Y$_1$ is hydrogen and Y is SONH$_2$.
In one embodiment, Y$_1$ is hydrogen and Y is SO$_2$NH$_2$.
In one embodiment, Y$_1$ is hydrogen and Y is —SONHR$_1$.
In one embodiment, Y$_1$ is hydrogen and Y is —SO$_2$NHR$_1$.
In one embodiment, Y$_1$ is hydrogen and Y is —COR$_1$.
In one embodiment, Y$_1$ is hydrogen and Y is —OR$_1$.
In one embodiment, Y$_1$ is hydrogen and Y is —R$_1$.
In one embodiment, Y$_1$ is hydrogen and Y is —CN.
In one embodiment, Y$_1$ is hydrogen and Y is -halo.
In one embodiment, Y$_1$ is hydrogen and Y is -phenyl optionally substituted with -halo, —NO$_2$, —SO$_2$CH$_3$, —R$_1$, or —OR$_1$.
In one embodiment, X is —CH$_3$ and X$_1$ is —CH$_3$.
In one embodiment, X is —CH$_3$ and X$_1$ is —CF$_3$.
In one embodiment, X is —CH$_3$ and X$_1$ is —OH.
In one embodiment, X is —CF$_3$ and X$_1$ is —CF$_3$.
In one embodiment, X is —CF$_3$ and X$_1$ is -halo.
In one embodiment, X is —CF$_3$ and X$_1$ is —Cl.
In one embodiment, X is —CF$_3$ and X$_1$ is —Br.
In one embodiment, X is —CF$_3$ and X$_1$ is —I.
In one embodiment, X is —CF$_3$ and X$_1$ is —F.
In one embodiment, X is —CF$_3$ and X$_1$ is —OH.
In one embodiment, X is —CH$_3$, X$_1$ is —CH$_3$, Y$_1$ is hydrogen, and Y is —NO$_2$.
In one embodiment, X is —CH$_3$, X$_1$ is —CH$_3$, Y$_1$ is hydrogen, and Y is —SO$_2$NH$_2$.
In one embodiment, X is —CH$_3$, X$_1$ is —OH, Y$_1$ is hydrogen, and Y is —NO$_2$.
In one embodiment, X is —CH$_3$, X$_1$ is —OH, Y$_1$ is hydrogen, and Y is —SO$_2$NH$_2$.
In one embodiment, X is —CH$_3$, X$_1$ is —CF$_3$, Y$_1$ is hydrogen, and Y is —NO$_2$.
In one embodiment, X is —CH$_3$, X$_1$ is —CF$_3$, Y$_1$ is hydrogen, and Y is —SO$_2$NH$_2$.
In one embodiment, X is —CF$_3$, X$_1$ is -halo, Y$_1$ is hydrogen, and Y is —NO$_2$.
In one embodiment, X is —CF$_3$, X$_1$ is -halo, Y$_1$ is hydrogen, and Y is —SO$_2$NH$_2$
In one embodiment, X is —CF$_3$, X$_1$ is —Cl, Y$_1$ is hydrogen, and Y is —NO$_2$.
In one embodiment, X is —CF$_3$, X$_1$ is —Cl, Y$_1$ is hydrogen, and Y is —SO$_2$NH$_2$.
In one embodiment, X is —CF$_3$, X$_1$ is —Br, Y$_1$ is hydrogen, and Y is —NO$_2$.
In one embodiment, X is —CF$_3$, X$_1$ is —Br, Y$_1$ is hydrogen, and Y is —SO$_2$NH$_2$.
In one embodiment, X is —CF$_3$, X$_1$ is —I, Y$_1$ is hydrogen, and Y is —NO$_2$.
In one embodiment, X is —CF$_3$, X$_1$ is —I, Y$_1$ is hydrogen, and Y is —SO$_2$NH$_2$.
In one embodiment, X is —CF$_3$, X$_1$ is —F, Y$_1$ is hydrogen, and Y is —NO$_2$.

In one embodiment, X is —CF$_3$, X$_1$ is —F, Y$_1$ is hydrogen, and Y is —SO$_2$NH$_2$.

In one embodiment, X is —CF$_3$, X$_1$ is —OH, Y$_1$ is hydrogen, and Y is —NO$_2$.

In one embodiment, X is —CF$_3$, X$_1$ is —OH, Y$_1$ is hydrogen, and Y is —SO$_2$NH$_2$.

In one embodiment, X is —CF$_3$, X$_1$ is —CF$_3$, Y$_1$ is hydrogen, and Y is —NO$_2$.

In one embodiment, X is —CF$_3$, X$_1$ is —CF$_3$, Y$_1$ is hydrogen, and Y is —SO$_2$NH$_2$.

The present invention also encompasses Fenicol Compounds of formula (Ia):

(Ia)

and pharmaceutically acceptable salts thereof, wherein
X is —CH$_3$ and X$_1$ is —CH$_3$, —CF$_3$, or —OH or
X is —CF$_3$ and X$_1$ is —CF$_3$; -halo, or —OH;
R$_2$ is a C$_1$ to C$_{18}$ hydrocarbon group that may optionally be substituted with a —NH$_2$ or —COOH;
Y and Y$^1$ is —H; —NO$_2$; —SO$_2$R$_1$; —SOR$_1$; —SR$_1$; —SONH$_2$; —SO$_2$NH$_2$; —SONHR$_1$; —SO$_2$NHR$_1$; —COR$_2$; —OR$_1$; —R$_1$; —CN, -halo; -phenyl; or -phenyl substituted with -halo, —NO$_2$, —SO$_2$CH$_3$, —R$_1$, or —OR$_1$;
R$_1$ is a C$_1$ to C$_3$ hydrocarbon group; and
halo is —Cl, —Br, —I, or —F.

In one embodiment, R$_2$ is a C$_1$ to C$_{18}$ hydrocarbon group substituted with a —NH$_2$ or —COOH.

In one embodiment, R$_2$ is an unsubstituted C$_1$ to C$_{18}$ hydrocarbon group.

In one embodiment, Z is acetyl.
In one embodiment, Z is butanoyl.
In one embodiment, Z is hexanoyl.
In one embodiment, Y$_1$ is hydrogen.
In one embodiment, Y$_1$ is hydrogen and Y is hydrogen.
In one embodiment, Y$_1$ is hydrogen and Y is —NO$_2$.
In one embodiment, Y$_1$ is hydrogen and Y is —SO$_2$R$_1$.
In one embodiment, Y$_1$ is hydrogen and Y is —SOR$_1$.
In one embodiment, Y$_1$ is hydrogen and Y is —SR$_1$.
In one embodiment, Y$_1$ is hydrogen and Y is SONH$_2$.
In one embodiment, Y$_1$ is hydrogen and Y is SO$_2$NH$_2$.
In one embodiment, Y$_1$ is hydrogen and Y is —SONHR$_1$.
In one embodiment, Y$_1$ is hydrogen and Y is —SO$_2$NHR$_1$.
In one embodiment, Y$_1$ is hydrogen and Y is —COR$_1$.
In one embodiment, Y$_1$ is hydrogen and Y is —OR$_1$.
In one embodiment, Y$_1$ is hydrogen and Y is —R$_1$.
In one embodiment, Y$_1$ is hydrogen and Y is —CN.
In one embodiment, Y$_1$ is hydrogen and Y is -halo.
In one embodiment, Y$_1$ is hydrogen and Y is -phenyl optionally substituted with -halo, —NO$_2$, —SO$_2$CH$_3$, —R$_1$, or —OR$_1$.
In one embodiment, Y$_1$ is hydrogen and Y —SO$_2$CH$_3$.
In one embodiment, X is —CH$_3$ and X$_1$ is —CH$_3$.

In one embodiment, X is —CH$_3$ and X$_1$ is —CF$_3$.
In one embodiment, X is —CH$_3$ and X$_1$ is —OH.
In one embodiment, X is —CF$_3$ and X$_1$ is —CF$_3$.
In one embodiment, X is —CF$_3$ and X$_1$ is -halo.
In one embodiment, X is —CF$_3$ and X$_1$ is —Cl.
In one embodiment, X is —CF$_3$ and X$_1$ is —Br.
In one embodiment, X is —CF$_3$ and X$_1$ is —I.
In one embodiment, X is —CF$_3$ and X$_1$ is —F.
In one embodiment, X is —CF$_3$ and X$_1$ is —OH.
In one embodiment, X is —CH$_3$, X$_1$ is —CH$_3$, Y$_1$ is hydrogen, and Y is —NO$_2$.
In one embodiment, X is —CH$_3$, X$_1$ is —CH$_3$, Y$_1$ is hydrogen, and Y is —SO$_2$NH$_2$.
In one embodiment, X is —CH$_3$, X$_1$ is —CH$_3$, Y$_1$ is hydrogen, and Y is —SO$_2$CH$_3$.
In one embodiment, X is —CH$_3$, X$_1$ is —OH, Y$_1$ is hydrogen, and Y is —NO$_2$.
In one embodiment, X is —CH$_3$, X$_1$ is —OH, Y$_1$ is hydrogen, and Y is —SO$_2$NH$_2$.
In one embodiment, X is —CH$_3$, X$_1$ is —OH, Y$_1$ is hydrogen, and Y is —SO$_2$CH$_3$.
In one embodiment, X is —CH$_3$, X$_1$ is —CF$_3$, Y$_1$ is hydrogen, and Y is —NO$_2$.
In one embodiment, X is —CH$_3$, X$_1$ is —CF$_3$, Y$_1$ is hydrogen, and Y is —SO$_2$NH$_2$.
In one embodiment, X is —CH$_3$, X$_1$ is —CF$_3$, Y$_1$ is hydrogen, and Y is —SO$_2$CH$_3$.
In one embodiment, X is —CF$_3$, X$_1$ is -halo, Y$_1$ is hydrogen, and Y is —NO$_2$.
In one embodiment, X is —CF$_3$, X$_1$ is -halo, Y$_1$ is hydrogen, and Y is —SO$_2$NH$_2$.
In one embodiment, X is —CF$_3$, X$_1$ is -halo, Y$_1$ is hydrogen, and Y is —SO$_2$CH$_3$.
In one embodiment, X is —CF$_3$, X$_1$ is —Cl, Y$_1$ is hydrogen, and Y is —NO$_2$.
In one embodiment, X is —CF$_3$, X$_1$ is —Cl, Y$_1$ is hydrogen, and Y is —SO$_2$NH$_2$.
In one embodiment, X is —CF$_3$, X$_1$ is —Cl, Y$_1$ is hydrogen, and Y is —SO$_2$CH$_3$.
In one embodiment, X is —CF$_3$, X$_1$ is —Br, Y$_1$ is hydrogen, and Y is —NO$_2$.
In one embodiment, X is —CF$_3$, X$_1$ is —Br, Y$_1$ is hydrogen, and Y is —SO$_2$NH$_2$.
In one embodiment, X is —CF$_3$, X$_1$ is —Br, Y$_1$ is hydrogen, and Y is —SO$_2$CH$_3$.
In one embodiment, X is —CF$_3$, X$_1$ is —I, Y$_1$ is hydrogen, and Y is —NO$_2$.
In one embodiment, X is —CF$_3$, X$_1$ is —I, Y$_1$ is hydrogen, and Y is —SO$_2$NH$_2$.
In one embodiment, X is —CF$_3$, X$_1$ is —I, Y$_1$ is hydrogen, and Y is —SO$_2$CH$_3$.
In one embodiment, X is —CF$_3$, X$_1$ is —F, Y$_1$ is hydrogen, and Y is —NO$_2$.
In one embodiment, X is —CF$_3$, X$_1$ is —F, Y$_1$ is hydrogen, and Y is —SO$_2$NH$_2$.
In one embodiment, X is —CF$_3$, X$_1$ is —F, Y$_1$ is hydrogen, and Y is —SO$_2$CH$_3$.
In one embodiment, X is —CF$_3$, X$_1$ is —OH, Y$_1$ is hydrogen, and Y is —NO$_2$.
In one embodiment, X is —CF$_3$, X$_1$ is —OH, Y$_1$ is hydrogen, and Y is —SO$_2$NH$_2$.
In one embodiment, X is —CF$_3$, X$_1$ is —OH, Y$_1$ is hydrogen, and Y is —SO$_2$CH$_3$.
In one embodiment, X is —CF$_3$, X$_1$ is —CF$_3$, Y$_1$ is hydrogen, and Y is —NO$_2$.
In one embodiment, X is —CF$_3$, X$_1$ is —CF$_3$, Y$_1$ is hydrogen, and Y is —SO$_2$NH$_2$.

In one embodiment, X is —CF₃, X₁ is —F, Y₁ is hydrogen, and Y is —SO₂CH₃.

5.2 Fenicol Compounds of Formula (II)

The present invention also relates to compounds of formula (II):

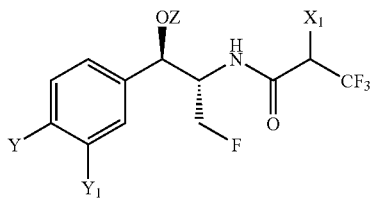

(II)

or a pharmaceutically acceptable salt thereof, wherein

X₁ is —CH₃, —CF₃; -halo, or —OH;

Z is hydrogen or an acyl group of formula —C(O)—R₂, wherein R₂ is a C₁ to C₁₈ hydrocarbon group that may optionally be substituted with a —NH₂ or —COOH;

Y and Y¹ is —H; —NO₂; —SO₂R₁; —SOR₁; —SR₁; —SONH₂; —SO₂NH₂; —SONHR₁; —SO₂NHR₁; —COR₁; —OR₁; —R₁; —CN, -halo; -phenyl; or -phenyl substituted with -halo, —NO₂, —SO₂CH₃, —R₁, or —OR₁;

R₁ is a C₁ to C₃ hydrocarbon group; and halo is —Cl, —Br, —I, or —F.

In one embodiment, Z is —H.

In one embodiment, Z is an acyl group of formula —C(O)—R₂, wherein R₂ is a C₁ to C₁₈ hydrocarbon group that may optionally be substituted with a —NH₂ or —COOH.

In one embodiment, Z is an acyl group of formula —C(O)—R₂, wherein R₂ is an unsubstituted C₁ to C₁₈ hydrocarbon group.

In one embodiment, Z is acetyl.
In one embodiment, Z is butanoyl.
In one embodiment, Z is hexanoyl.
In one embodiment, Y₁ is hydrogen.
In one embodiment, Y₁ is hydrogen and Y is hydrogen.
In one embodiment, Y₁ is hydrogen and Y is —NO₂.
In one embodiment, Y₁ is hydrogen and Y is —SO₂R.
In one embodiment, Y₁ is hydrogen and Y is —SOR₁.
In one embodiment, Y₁ is hydrogen and Y is —SR₁.
In one embodiment, Y₁ is hydrogen and Y is SONH₂.
In one embodiment, Y₁ is hydrogen and Y is SO₂NH₂.
In one embodiment, Y₁ is hydrogen and Y is —SONHR₁.
In one embodiment, Y₁ is hydrogen and Y is —SO₂NHR₁.
In one embodiment, Y₁ is hydrogen and Y is —COR₁.
In one embodiment, Y₁ is hydrogen and Y is —OR₁.
In one embodiment, Y₁ is hydrogen and Y is —R₁.
In one embodiment, Y₁ is hydrogen and Y is —CN.
In one embodiment, Y₁ is hydrogen and Y is -halo.
In one embodiment, Y₁ is hydrogen and Y is -phenyl optionally substituted with -halo, —NO₂, —SO₂CH₃, —R₁, or —OR₁.
In one embodiment, Y₁ is hydrogen and Y —SO₂CH₃.
In one embodiment, Z is hydrogen and X₁ is —CH₃.
In one embodiment, Z is hydrogen and X₁ is —CF₃.
In one embodiment, Z is hydrogen and X₁ is -halo.
In one embodiment, Z is hydrogen and X₁ is —Cl.
In one embodiment, Z is hydrogen and X₁ is —Br.
In one embodiment, Z is hydrogen and X₁ is —I.
In one embodiment, Z is hydrogen and X₁ is —F.
In one embodiment, Z is hydrogen, X₁ is —CH₃, Y₁ is hydrogen, and Y is —SO₂CH₃.
In one embodiment, Z is hydrogen, X₁ is —CH₃, Y₁ is hydrogen, and Y is —NO₂.
In one embodiment, Z is hydrogen, X₁ is —CH₃, Y₁ is hydrogen, and Y is —SO₂NH₂.
In one embodiment, Z is hydrogen, X₁ is -halo, Y₁ is hydrogen, and Y is —SO₂CH₃.
In one embodiment, Z is hydrogen, X₁ is -halo, Y₁ is hydrogen, and Y is —NO₂.
In one embodiment, Z is hydrogen, X₁ is -halo, Y₁ is hydrogen, and Y is —SO₂NH₂.
In one embodiment, Z is hydrogen, X₁ is —Cl, Y₁ is hydrogen, and Y is —SO₂CH₃.
In one embodiment, Z is hydrogen, X₁ is —Cl, Y₁ is hydrogen, and Y is —NO₂.
In one embodiment, Z is hydrogen, X₁ is —Cl, Y₁ is hydrogen, and Y is —SO₂NH₂.
In one embodiment, Z is hydrogen, X₁ is —Br, Y₁ is hydrogen, and Y is —SO₂CH₃.
In one embodiment, Z is hydrogen, X₁ is —Br, Y₁ is hydrogen, and Y is —NO₂.
In one embodiment, Z is hydrogen, X₁ is —Br, Y₁ is hydrogen, and Y is —SO₂NH₂.
In one embodiment, Z is hydrogen, X₁ is —I, Y₁ is hydrogen, and Y is —SO₂CH₃.
In one embodiment, Z is hydrogen, X₁ is —I, Y₁ is hydrogen, and Y is —NO₂.
In one embodiment, Z is hydrogen, X₁ is —I, Y₁ is hydrogen, and Y is —SO₂NH₂.
In one embodiment, Z is hydrogen, X₁ is —F, Y₁ is hydrogen, and Y is —SO₂CH₃.
In one embodiment, Z is hydrogen, X₁ is —F, Y₁ is hydrogen, and Y is —NO₂.
In one embodiment, Z is hydrogen, X₁ is —F, Y₁ is hydrogen, and Y is —SO₂NH₂.
In one embodiment, Z is hydrogen, X₁ is —OH, Y₁ is hydrogen, and Y is —SO₂CH₃.
In one embodiment, Z is hydrogen, X₁ is —OH, Y₁ is hydrogen, and Y is —NO₂.
In one embodiment, Z is hydrogen, X₁ is —OH, Y₁ is hydrogen, and Y is —SO₂NH₂.
In one embodiment, Z is hydrogen, X₁ is —CF₃, Y₁ is hydrogen, and Y is —SO₂CH₃.
In one embodiment, Z is hydrogen, X₁ is —CF₃, Y₁ is hydrogen, and Y is —NO₂.
In one embodiment, Z is hydrogen, X₁ is —CF₃, Y₁ is hydrogen, and Y is —SO₂NH₂.
In one embodiment, Z is an acyl group of formula —C(O)—R₂, wherein R₂ is a C₁ to C₁₈ hydrocarbon group that may optionally be substituted with a —NH₂ or —COOH, Y₁ is hydrogen, and Y is —NO₂, —SO₂CH₃, or —SONH₂.
In one embodiment, Z is an acyl group of formula —C(O)—R₂, wherein R₂ is a C₁ to C₁₈ hydrocarbon group that may optionally be substituted with a —NH₂ or —COOH, Y₁ is hydrogen, and Y is —NO₂.
In one embodiment, Z is an acyl group of formula —C(O)—R₂, wherein R₂ is a C₁ to C₁₈ hydrocarbon group that may optionally be substituted with a —NH₂ or —COOH, Y₁ is hydrogen, and Y is —SO₂CH₃.
In one embodiment, Z is an acyl group of formula —C(O)—R₂, wherein R₂ is a C₁ to C₁₈ hydrocarbon group that may optionally be substituted with a —NH₂ or —COOH, Y₁ is hydrogen and Y is —SO₂NH₂.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH and $X_1$ is —$CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH and $X_1$ is —$CF_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH and $X_1$ is -halo.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH and $X_1$ is —Cl.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH and $X_1$ is —Br.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH and $X_1$ is —I.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH and $X_1$ is —F.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH and $X_1$ is —OH.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —$CH_3$, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —$CH_3$, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —$CH_3$, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is -halo, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is -halo, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is -halo, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —Cl, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —Cl, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —Cl, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —Br, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —Br, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —Br, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —I, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —I, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —I, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —F, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —F, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —F, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —OH, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —OH, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —OH, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —$CF_3$, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —$CF_3$, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $X_1$ is —$CF_3$, $Y_1$ is hydrogen, and Y is —$SO_2NH_2$.

5.3 Fenicol Compounds of Formula (D)

The present invention also relates to compounds of formula (III)

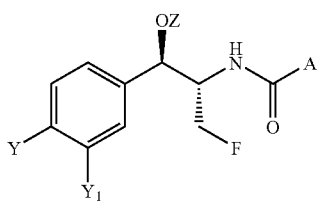
(III)

and pharmaceutically acceptable salts thereof,
wherein
A is (R) —CH($CH_3$)($CF_3$) substantially free of (S) —CH($CH_3$)($CF_3$), (R) —CH($CH_3$)(halo) substantially free of (S) —CH($CH_3$)(halo), (R) —CH($CF_3$)(halo) substantially free of (S) —CH($CF_3$)(halo), (R) —CH($CF_3$)(OH) substantially free of (S) —CH($CF_3$)(OH), (S) —CH($CH_3$)($CF_3$) substantially free of (R) —CH($CH_3$)($CF_3$), (S) —CH($CH_3$)(halo) substantially free of (R) —CH($CH_3$)(halo), (S) —CH($CF_3$)(halo) substantially free of (R) —CH($CF_3$)(halo), or (S) —CH($CF_3$)(OH) substantially free of (R) —CH($CF_3$)(OH);
Z is hydrogen or an acyl group of formula —C(O)—$R_2$, wherein $R_2$ is a $C_1$ to $C_{18}$ hydrocarbon group that may optionally be substituted with a —$NH_2$ or —COOH;
Y and $Y^1$ is —H; —$NO_2$; —$SO_2R_1$; —$SOR_1$; —$SR_1$; —$SONH_2$; —$SO_2NH_2$; —$SONHR_1$; —$SO_2NHR_1$; —$COR_2$; —$OR_1$; —$R_1$; —CN, -halogen; -phenyl; or -phenyl substituted with -halogen, —$NO_2$, —$SO_2CH_3$, —$R_1$, or —$OR_1$;
halo is —Cl, —Br, —I, or —F; and
$R_1$ is a $C_1$ to $C_3$ hydrocarbon group.

In one embodiment, Z is hydrogen.
In one embodiment, $Y_1$ is hydrogen.
In one embodiment, Z is an acyl hydrocarbon of formula —C(O)—$R_2$, wherein $R_2$ is a $C_1$ to $C_{18}$ group that may optionally be substituted with a —$NH_2$ or —COOH.
In one embodiment, Z is an acyl group of formula —C(O)—$R_2$, wherein $R_2$ is an unsubstituted $C_1$ to $C_{18}$ hydrocarbon group.
In one embodiment, A has the (R)-configuration.
In one embodiment, A has the (S)-configuration.
In one embodiment, A is (R) —CH($CH_3$)($CF_3$).
In one embodiment, A is (R) —CH($CH_3$)(halo).
In one embodiment, A is (R) —CH($CH_3$)(Cl).
In one embodiment, A is (R) —CH($CH_3$)(Br).
In one embodiment, A is (R) —CH($CH_3$)(I).
In one embodiment, A is (R) —CH($CH_3$)(F).
In one embodiment, A is (R) —CH($CH_3$)(OH).
In one embodiment, A is (R) —CH($CF_3$)(halo).
In one embodiment, A is (R) —CH($CF_3$)(Cl).
In one embodiment, A is (R) —CH($CF_3$)(Br).
In one embodiment, A is (R) —CH($CF_3$)(I).
In one embodiment, A is (R) —CH($CF_3$)(F).
In one embodiment, A is (R) —CH($CF_3$)(OH).
In one embodiment, A is (S) —CH($CH_3$)($CF_3$).
In one embodiment, A is (S) —CH($CH_3$)(halo).
In one embodiment, A is (S) —CH($CH_3$)(Cl).
In one embodiment, A is (S) —CH($CH_3$)(Br).
In one embodiment, A is (S) —CH($CH_3$)(I).
In one embodiment, A is (S) —CH($CH_3$)(F).
In one embodiment, A is (S) —CH($CH_3$)(OH).
In one embodiment, A is (S) —CH($CF_3$)(halo).
In one embodiment, A is (S) —CH($CF_3$)(Cl).
In one embodiment, A is (S) —CH($CF_3$)(Br).
In one embodiment, A is (S) —CH($CF_3$)(I).
In one embodiment, A is (S) —CH($CF_3$)(F).
In one embodiment, A is (S) —CH($CF_3$)(OH).
In one embodiment, Z is hydrogen, $Y_1$ is hydrogen, and Y is —$NO_2$, —$SO_2CH_3$, or —$SO_2NH_2$.
In one embodiment, Z is hydrogen, $Y_1$ is hydrogen, and Y is —$NO_2$.
In one embodiment, Z is hydrogen, $Y_1$ is hydrogen, and Y is —$SO_2CH_3$.
In one embodiment, Z is hydrogen, $Y_1$ is hydrogen, and Y is —$SO_2NH_2$.
In one embodiment, Z is hydrogen and A is (R) —CH($CH_3$)($CF_3$).
In one embodiment, Z is hydrogen, A is (R) —CH($CH_3$)(halo).
In one embodiment, Z is hydrogen and A is (R) —CH($CH_3$)(Cl).
In one embodiment, Z is hydrogen and A is (R) —CH($CH_3$)(Br).
In one embodiment, Z is hydrogen and A is (R) —CH($CH_3$)(I).
In one embodiment, Z is hydrogen and A is (R) —CH($CH_3$)(F).
In one embodiment, Z is hydrogen and A is (R) —CH($CH_3$)(OH).
In one embodiment, Z is hydrogen and A is (R) —CH($CF_3$)(halo).
In one embodiment, Z is hydrogen and A is (R) —CH($CF_3$)(Cl).
In one embodiment, Z is hydrogen and A is (R) —CH($CF_3$)(Br).
In one embodiment, Z is hydrogen and A is (R) —CH($CF_3$)(I).
In one embodiment, Z is hydrogen and A is (R) —CH($CF_3$)(F).
In one embodiment, Z is hydrogen and A is (R) —CH($CF_3$)(OH).
In one embodiment, Z is hydrogen and A is (S) —CH($CH_3$)($CF_3$).
In one embodiment, Z is hydrogen and A is (S) —CH($CH_3$)(halo).
In one embodiment, Z is hydrogen and A is (S) —CH($CH_3$)(Cl).
In one embodiment, Z is hydrogen and A is (S) —CH($CH_3$)(Br).
In one embodiment, Z is hydrogen and A is (S) —CH($CH_3$)(I).
In one embodiment, Z is hydrogen and A is (S) —CH($CH_3$)(F).
In one embodiment, Z is hydrogen and A is (S) —CH($CH_3$)(OH).
In one embodiment, Z is hydrogen and A is (S) —CH($CF_3$)(halo).
In one embodiment, Z is hydrogen and A is (S) —CH($CF_3$)(Cl).
In one embodiment, Z is hydrogen and A is (S) —CH($CF_3$)(Br).
In one embodiment, Z is hydrogen and A is (S) —CH($CF_3$)(I).
In one embodiment, Z is hydrogen and A is (S) —CH($CF_3$)(F).
In one embodiment, Z is hydrogen and A is (S) —CH($CF_3$)(OH).
In one embodiment, Z is hydrogen, $Y_1$ is hydrogen, Y is —$SO_2CH_3$, and A is (R) —H($CH_3$)($CF_3$).

In one embodiment, Z is hydrogen, $Y_1$ is hydrogen, Y is —SO$_2$CH$_3$, and A is (R) —CH(CH$_3$)(halo).
In one embodiment, Z is hydrogen, $Y_1$ is hydrogen, Y is —SO$_2$CH$_3$, and A is (R) —CH(CH$_3$)(Cl).
In one embodiment, Z is hydrogen, $Y_1$ is hydrogen, Y is —SO$_2$CH$_3$, and A is (R) —CH(CH$_3$)(Br).
In one embodiment, Z is hydrogen, $Y_1$ is hydrogen, Y is —SO$_2$CH$_3$, and A is (R) —CH(CH$_3$)(I).
In one embodiment, Z is hydrogen, $Y_1$ is hydrogen, Y is —SO$_2$CH$_3$, and A is (R) —CH(CH$_3$)(F).
In one embodiment, Z is hydrogen, $Y_1$ is hydrogen, Y is —SO$_2$CH$_3$, and A is (R) —CH(CH$_3$)(OH).
In one embodiment, Z is hydrogen, $Y_1$ is hydrogen, Y is —SO$_2$CH$_3$, and A is (R) —CH(CF$_3$)(halo).
In one embodiment, Z is hydrogen, $Y_1$ is hydrogen, Y is —SO$_2$CH$_3$, and A is (R) —CH(CF$_3$)(CL).
In one embodiment, Z is hydrogen, $Y_1$ is hydrogen, Y is —SO$_2$CH$_3$, and A is (R) —CH(CF$_3$)(Br).
In one embodiment, Z is hydrogen, $Y_1$ is hydrogen, Y is —SO$_2$CH$_3$, and A is (R) —CH(CF$_3$)(I).
In one embodiment, Z is hydrogen, $Y_1$ is hydrogen, Y is —SO$_2$CH$_3$, and A is (R) —CH(CF$_3$)(F).
In one embodiment, Z is hydrogen, $Y_1$ is hydrogen, Y is —SO$_2$CH$_3$, and A is (R) —CH(CF$_3$)(OH).
In one embodiment, Z is hydrogen, $Y_1$ is hydrogen, Y is —SO$_2$CH$_3$, and A is (S) —CH(CH$_3$)(CF$_3$).
In one embodiment, Z is hydrogen, $Y_1$ is hydrogen, Y is —SO$_2$CH$_3$, and A is (S) —CH(CH$_3$)(halo).
In one embodiment, Z is hydrogen, $Y_1$ is hydrogen, Y is —SO$_2$CH$_3$, and A is (S) —CH(CH$_3$)(Cl).
In one embodiment, Z is hydrogen, $Y_1$ is hydrogen, Y is —SO$_2$CH$_3$, and A is (S) —CH(CH$_3$)(Br).
In one embodiment, Z is hydrogen, $Y_1$ is hydrogen, Y is —SO$_2$CH$_3$, and A is (S) —CH(CH$_3$)(I).
In one embodiment, Z is hydrogen, $Y_1$ is hydrogen, Y is —SO$_2$CH$_3$, and A is (S) —CH(CH$_3$)(F).
In one embodiment, Z is hydrogen, $Y_1$ is hydrogen, Y is —SO$_2$CH$_3$, and A is (S) —CH(CH$_3$)(OH).
In one embodiment, Z is hydrogen, $Y_1$ is hydrogen, Y is —SO$_2$CH$_3$, and A is (S) —CH(CF$_3$)(halo).
In one embodiment, Z is hydrogen, $Y_1$ is hydrogen, Y is —SO$_2$CH$_3$, and A is (S) —CH(CF$_3$)(Cl).
In one embodiment, Z is hydrogen, $Y_1$ is hydrogen, Y is —SO$_2$CH$_3$, and A is (S) —CH(CF$_3$)(Br).
In one embodiment, Z is hydrogen, $Y_1$ is hydrogen, Y is —SO$_2$CH$_3$, and A is (S) —CH(CF$_3$)(I).
In one embodiment, Z is hydrogen, $Y_1$ is hydrogen, Y is —SO$_2$CH$_3$, and A is (S) —CH(CF$_3$)(F).
In one embodiment, Z is hydrogen, $Y_1$ is hydrogen, Y is —SO$_2$CH$_3$, and A is (S) —CH(CF$_3$)(OH).
In one embodiment, Z is hydrogen, $Y_1$ is hydrogen, Y is —NO$_2$, and A is (R) —CH(CH$_3$)(CF$_3$).
In one embodiment, Z is hydrogen, $Y_1$ is hydrogen, Y is —NO$_2$, and A is (R) —CH(CH$_3$)(halo).
In one embodiment, Z is hydrogen, $Y_1$ is hydrogen, Y is —NO$_2$, and A is (R) —CH(CH$_3$)(Cl).
In one embodiment, Z is hydrogen, $Y_1$ is hydrogen, Y is —NO$_2$, and A is (R) —CH(CH$_3$)(Br).
In one embodiment, Z is hydrogen, $Y_1$ is hydrogen, Y is —NO$_2$, and A is (R) —CH(CH$_3$)(I).
In one embodiment, Z is hydrogen, $Y_1$ is hydrogen, Y is —NO$_2$, and A is (R) —CH(CH$_3$)(F).
In one embodiment, Z is hydrogen, $Y_1$ is hydrogen, Y is —NO$_2$, and A is (R) —CH(CH$_3$)(OH).
In one embodiment, Z is hydrogen, $Y_1$ is hydrogen, Y is —NO$_2$, and A is (R) —CH(CF$_3$)(halo).
In one embodiment, Z is hydrogen, $Y_1$ is hydrogen, Y is —NO$_2$, and A is (R) —CH(CF$_3$)(Cl).
In one embodiment, Z is hydrogen, $Y_1$ is hydrogen, Y is —NO$_2$, and A is (R) —CH(CF$_3$)(Br).
In one embodiment, Z is hydrogen, $Y_1$ is hydrogen, Y is —NO$_2$, and A is (R) —CH(CF$_3$)(I).
In one embodiment, Z is hydrogen, $Y_1$ is hydrogen, Y is —NO$_2$, and A is (R) —CH(CF$_3$)(F).
In one embodiment, Z is hydrogen, $Y_1$ is hydrogen, Y is —NO$_2$, and A is (R) —CH(CF$_3$)(OH).
In one embodiment, Z is hydrogen, $Y_1$ is hydrogen, Y is —NO$_2$, and A is (S) —CH(CH$_3$)(CF$_3$).
In one embodiment, Z is hydrogen, $Y_1$ is hydrogen, Y is —NO$_2$, and A is (S) —CH(CH$_3$)(halo).
In one embodiment, Z is hydrogen, $Y_1$ is hydrogen, Y is —NO$_2$, and A is (S) —CH(CH$_3$)(Cl).
In one embodiment, Z is hydrogen, $Y_1$ is hydrogen, Y is —NO$_2$, and A is (S) —CH(CH$_3$)(Br).
In one embodiment, Z is hydrogen, $Y_1$ is hydrogen, Y is —NO$_2$, and A is (S) —CH(CH$_3$)(I).
In one embodiment, Z is hydrogen, $Y_1$ is hydrogen, Y is —NO$_2$, and A is (S) —CH(CH$_3$)(F).
In one embodiment, Z is hydrogen, $Y_1$ is hydrogen, Y is —NO$_2$, and A is (S) —CH(CH$_3$)(OH).
In one embodiment, Z is hydrogen, $Y_1$ is hydrogen, Y is —NO$_2$, and A is (S) —CH(CF$_3$)(halo).
In one embodiment, Z is hydrogen, $Y_1$ is hydrogen, Y is —NO$_2$, and A is (S) —CH(CF$_3$)(Cl).
In one embodiment, Z is hydrogen, $Y_1$ is hydrogen, Y is —NO$_2$, and A is (S) —CH(CF$_3$)(Br).
In one embodiment, Z is hydrogen, $Y_1$ is hydrogen, Y is —NO$_2$, and A is (S) —CH(CF$_3$)(I).
In one embodiment, Z is hydrogen, $Y_1$ is hydrogen, Y is —NO$_2$, and A is (S) —CH(CF$_3$)(F).
In one embodiment, Z is hydrogen, $Y_1$ is hydrogen, Y is —NO$_2$, and A is (S) —CH(CF$_3$)(OH)
In one embodiment, Z is hydrogen, $Y_1$ is hydrogen, Y is —SO$_2$NH$_2$, and A is (R) —CH(CH$_3$)(CF$_3$).
In one embodiment, Z is hydrogen, $Y_1$ is hydrogen, Y is —SO$_2$NH$_2$, and A is (R) —CH(CH$_3$)(halo).
In one embodiment, Z is hydrogen, $Y_1$ is hydrogen, Y is —SO$_2$NH$_2$, and A is (R) —CH(CH$_3$)(Cl).
In one embodiment, Z is hydrogen, $Y_1$ is hydrogen, Y is —SO$_2$NH$_2$, and A is (R) —CH(CH$_3$)(Br).
In one embodiment, Z is hydrogen, $Y_1$ is hydrogen, Y is —SO$_2$NH$_2$, and A is (R) —CH(CH$_3$)(I).
In one embodiment, Z is hydrogen, $Y_1$ is hydrogen, Y is —SO$_2$NH$_2$, and A is (R) —CH(CH$_3$)(F).
In one embodiment, Z is hydrogen, $Y_1$ is hydrogen, Y is —SO$_2$NH$_2$, and A is (R) —CH(CH$_3$)(OH).
In one embodiment, Z is hydrogen, $Y_1$ is hydrogen, Y is —SO$_2$NH$_2$, and A is (R) —CH(CF$_3$)(halo).
In one embodiment, Z is hydrogen, $Y_1$ is hydrogen, Y is —SO$_2$NH$_2$, and A is (R) —CH(CF$_3$)(Cl).
In one embodiment, Z is hydrogen, $Y_1$ is hydrogen, Y is —SO$_2$NH$_2$, and A is (R) —CH(CF$_3$)(Br).
In one embodiment, Z is hydrogen, $Y_1$ is hydrogen, Y is —SO$_2$NH$_2$, and A is (R) —CH(CF$_3$)(I)
In one embodiment, Z is hydrogen, $Y_1$ is hydrogen, Y is —SO$_2$NH$_2$, and A is (R) —CH(CF$_3$)(F).
In one embodiment, Z is hydrogen, $Y_1$ is hydrogen, Y is —SO$_2$NH$_2$, and A is (R) —CH(CF$_3$)(OH).
In one embodiment, Z is hydrogen, $Y_1$ is hydrogen, Y is —SO$_2$NH$_2$, and A is (S) —CH(CH$_3$)(CF$_3$).
In one embodiment, Z is hydrogen, $Y_1$ is hydrogen, Y is —SO$_2$NH$_2$, and A is (S) —CH(CH$_3$)(halo).

In one embodiment, Z is hydrogen, $Y_1$ is hydrogen, Y is —$SO_2NH_2$, and A is (S) —$CH(CH_3)(Cl)$.

In one embodiment, Z is hydrogen, $Y_1$ is hydrogen, Y is —$SO_2NH_2$, and A is (S) —$CH(CH_3)(Br)$.

In one embodiment, Z is hydrogen, $Y_1$ is hydrogen, Y is —$SO_2NH_2$, and A is (S) —$CH(CH_3)(I)$.

In one embodiment, Z is hydrogen, $Y_1$ is hydrogen, Y is —$SO_2NH_2$, and A is (S) —$CH(CH_3)(F)$.

In one embodiment, Z is hydrogen, $Y_1$ is hydrogen, Y is —$SO_2NH_2$, and A is (S) —$CH(CH_3)(OH)$.

In one embodiment, Z is hydrogen, $Y_1$ is hydrogen, Y is —$SO_2NH_2$, and A is (S) —$CH(CF_3)(halo)$.

In one embodiment, Z is hydrogen, $Y_1$ is hydrogen, Y is —$SO_2NH_2$, and A is (S) —$CH(CF_3)(Cl)$.

In one embodiment, Z is hydrogen, $Y_1$ is hydrogen, Y is —$SO_2NH_2$, and A is (S) —$CH(CF_3)(Br)$.

In one embodiment, Z is hydrogen, $Y_1$ is hydrogen, Y is —$SO_2NH_2$, and A is (S) —$CH(CF_3)(I)$.

In one embodiment, Z is hydrogen, $Y_1$ is hydrogen, Y is —$SO_2NH_2$, and A is (S) —$CH(CF_3)(F)$.

In one embodiment, Z is hydrogen, $Y_1$ is hydrogen, Y is —$SO_2NH_2$, and A is (S) —$CH(CF_3)(OH)$.

In one embodiment, Z is an acyl hydrocarbon of formula —$C(O)$—$R_2$, wherein $R_2$ is a $C_1$ to $C_{18}$ hydrocarbon group that may optionally be substituted with a —$NH_2$ or —COOH, $Y_1$ is hydrogen, and Y is —$NO_2$, —$SO_2CH_3$, or —$SO_2NH_2$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, $Y_1$ is hydrogen, and Y is —$NO_2$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, $Y_1$ is hydrogen, and Y is —$SO_2CH_3$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, $Y_1$ is hydrogen, and Y is —$SO_2NH_2$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CH_3)(halo)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CH_3)(Cl)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CH_3)(Br)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CH_3)(I)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CH_3)(F)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CH_3)(OH)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CF_3)(halo)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CF_3)(Cl)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CF_3)(Br)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CF_3)(I)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CF_3)(F)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CF_3)(OH)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (R) —$CH(CH_3)(CF_3)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CH_3)(halo)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CH_3)(Cl)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CH_3)(Br)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CH_3)(I)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CH_3)(F)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CH_3)(OH)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CF_3)(halo)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CF_3)(Cl)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CF_3)(Br)$.

In one embodiment, Z is an acyl group of formula —$C(O)$—$R_2$, wherein $R_2$ is a $C_1$ to $C_{18}$ hydrocarbon group that may optionally be substituted with a —$NH_2$ or —COOH, and A is (S) —$CH(CF_3)(I)$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, and A is (S) —CH($CF_3$)(F).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, and A is (S) —CH($CF_3$)(OH).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, and A is (S) —CH($CH_3$)($CF_3$).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CH_3$)($CF_3$).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CH_3$)(halo).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CH_3$)(Cl).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CH_3$)(Br).

In one embodiment, Z is an acyl group of formula —C(O)—$R_2$, wherein $R_2$ is a $C_1$ to $C_{18}$ group that may optionally be substituted with a —$NH_2$ or —COOH, $Y_1$ is hydrogen, Y is —$SO_2CH_3$, and A is (R) —CH($CH_3$)(I).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CH_3$)(F).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CH_3$)(OH).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CF_3$)(halo).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CF_3$)(Cl).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CF_3$)(Br).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CF_3$)(I).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CF_3$)(F).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (R) —CH($CF_3$)(OH).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CH_3$)($CF_3$).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CH_3$)(halo).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CH_3$)(Cl).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CH_3$)(Br).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CH_3$)(I).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CH_3$)(F).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CH_3$)(OH).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CF_3$)(halo).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CF_3$)(Cl).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CF_3$)(Br).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $YY_1^1$ is hydrogen, Y is —$SO_2CH_3$, and A is (S) —CH($CF_3$)(I).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CF_3$)(F).

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, Y is —$SO_2CH_3$, and A is (S) —CH($CF_3$)(OH).

In one embodiment, Z is an acyl group of formula —C(O)—$R_2$, wherein $R_2$ is a $C_1$ to $C_{18}$ hydrocarbon group that may optionally be substituted with a —NH$_2$ or —COOH, Y$_1$ is hydrogen, Y is —NO$_2$, and A is (R) —CH(CH$_3$)(CF$_3$).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CH$_3$)(halo).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CH$_3$)(Cl).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CH$_3$)(Br).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CH$_3$)(I).

In one embodiment, Z is an acyl group of formula —C(O)—R$_2$, wherein R$_2$ is a C$_1$ to C$_{18}$ group that may optionally be substituted with a —NH$_2$ or —COOH, Y$_1$ is hydrogen, Y is —NO$_2$, and A is (R) —CH(CH$_3$)(F).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CH$_3$)(OH).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CF$_3$)(halo).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CF$_3$)(Cl).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CF$_3$)(Br).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CF$_3$)(I).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CF$_3$)(F).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (R) —CH(CF$_3$)(OH).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CH$_3$)(CF$_3$).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CH$_3$)(halo).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$^1$ is hydrogen, Y is —NO$_2$, and A is (S) —CH(CH$_3$)(Cl).

In one embodiment, Z is an acyl group of formula —C(O)—R$_2$, wherein R$_2$ is a C$_1$ to C$_{18}$ group that may optionally be substituted with a —NH$_2$ or —COOH, Y$_1$ is hydrogen, Y is —NO$_2$, and A is (S) —CH(CH$_3$)(Br).

In one embodiment, Z is an acyl group of formula —C(O)—R$_2$, wherein R$_2$ is a C$_1$ to C$_{18}$ group that may optionally be substituted with a —NH$_2$ or —COOH, Y$_1$ is hydrogen, Y is —NO$_2$, and A is (S) —CH(CH$_3$)(I).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CH$_3$)(F).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CH$_3$)(OH).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CF$_3$)(halo).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CF$_3$)(Cl).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CF$_3$)(Br).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CF$_3$)(I).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CF$_3$)(F).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —NO$_2$, and A is (S) —CH(CF$_3$)(OH).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CH$_3$)(CF$_3$).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CH$_3$)(halo).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CH$_3$)(Cl).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CH$_3$)(Br).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CH$_3$)(I).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CH$_3$)(F).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CH$_3$)(OH).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CF$_3$)(halo).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CF$_3$)(Cl).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CF$_3$)(Br).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CF$_3$)(I).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CF$_3$)(F).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (R) —CH(CF$_3$)(OH).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CH$_3$)(CF$_3$).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CH$_3$)(halo).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CH$_3$)(Cl).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CH$_3$)(Br).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CH$_3$)(I).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CH$_3$)(F).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CH$_3$)(OH).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CF$_3$)(halo).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CF$_3$)(Cl).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CF$_3$)(Br).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$ is hydrogen, Y is —SO$_2$NH$_2$, and A is (S) —CH(CF$_3$)(I).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y, Y$_1$ is hydrogen, Y is —SO$_2$NH$_2$, and A is (S) —CH(CF$_3$)(F).

In one embodiment, Z is an acyl group of formula —C(O)—R$_2$, wherein R$_2$ is a C$_1$ to C$_{18}$ hydrocarbon group that may optionally be substituted with a —NH$_2$ or —COOH, Y$_1$Y$_1$ is hydrogen, Y is —SO$_2$NH$_2$, and A is (S) —CH(CF$_3$)(OH).

5.4 Illustrative Fenicol Compounds

Illustrative Fenicol Compounds useful in the compositions and methods of the invention are listed below in Tables A-L.

TABLE A

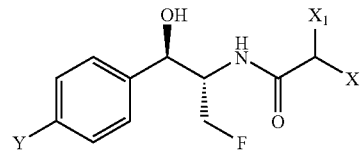

| Compound | Y | X$_1$ | X |
|---|---|---|---|
| A1 | —SO$_2$CH$_3$ | —CH$_3$ | —CH$_3$ |
| A2 | —SO$_2$CH$_3$ | —CH$_3$ | —CF$_3$ |
| A3 | —SO$_2$CH$_3$ | —CF$_3$ | —CF$_3$ |
| A4 | —SO$_2$CH$_3$ | —CF$_3$ | —Cl |
| A5 | —SO$_2$CH$_3$ | —CF$_3$ | —Br |
| A6 | —SO$_2$CH$_3$ | —CF$_3$ | —I |
| A7 | —SO$_2$CH$_3$ | —CF$_3$ | —F |
| A8 | —SO$_2$CH$_3$ | —CH$_3$ | —OH |
| A9 | —SO$_2$CH$_3$ | —CF$_3$ | —OH |
| A10 | —NO$_2$ | —CH$_3$ | —CH$_3$ |
| A11 | —NO$_2$ | —CH$_3$ | —CF$_3$ |
| A12 | —NO$_2$ | —CF$_3$ | —CF$_3$ |
| A13 | —NO$_2$ | —CF$_3$ | —Cl |
| A14 | —NO$_2$ | —CF$_3$ | —Br |
| A15 | —NO$_2$ | —CF$_3$ | —I |
| A16 | —NO$_2$ | —CH$_3$ | —F |
| A17 | —NO$_2$ | —CH$_3$ | —OH |
| A18 | —NO$_2$ | —CF$_3$ | —OH |
| A19 | —SO$_2$NH$_2$ | —CF$_3$ | —CH$_3$ |
| A20 | —SO$_2$NH$_2$ | —CH$_3$ | —CF$_3$ |
| A21 | —SO$_2$NH$_2$ | —CF$_3$ | —CF$_3$ |
| A22 | —SO$_2$NH$_2$ | —CF$_3$ | —Cl |
| A23 | —SO$_2$NH$_2$ | —CF$_3$ | —Br |
| A24 | —SO$_2$NH$_2$ | —CF$_3$ | —I |
| A25 | —SO$_2$NH$_2$ | —CF$_3$ | —F |
| A26 | —SO$_2$NH$_2$ | —CH$_3$ | —OH |
| A27 | —SO$_2$NH$_2$ | —CF$_3$ | —OH |

TABLE B

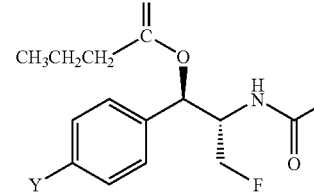

| Compound | Y | X₁ | X |
|---|---|---|---|
| B1 | —SO₂CH₃ | —CH₃ | —CH₃ |
| B2 | —SO₂CH₃ | —CH₃ | —CF₃ |
| B3 | —SO₂CH₃ | —CF₃ | —CF₃ |
| B4 | —SO₂CH₃ | —CF₃ | —Cl |
| B5 | —SO₂CH₃ | —CF₃ | —Br |
| B6 | —SO₂CH₃ | —CF₃ | —I |
| B7 | —SO₂CH₃ | —CF₃ | —F |
| B8 | —SO₂CH₃ | —CH₃ | —OH |
| B9 | —SO₂CH₃ | —CF₃ | —OH |
| B10 | —NO₂ | —CH₃ | —CH₃ |
| B11 | —NO₂ | —CH₃ | —CF₃ |
| B12 | —NO₂ | —CF₃ | —CF₃ |
| B13 | —NO₂ | —CF₃ | —Cl |
| B14 | —NO₂ | —CF₃ | —Br |
| B15 | —NO₂ | —CF₃ | —I |
| B16 | —NO₂ | —CF₃ | —F |
| B17 | NO₂ | —CH₃ | —OH |
| B18 | NO₂ | —CF₃ | —OH |
| B19 | —SO₂NH₂ | —CH₃ | —CH₃ |
| B20 | —SO₂NH₂ | —CH₃ | —CF₃ |
| B21 | —SO₂NH₂ | —CF₃ | —CF₃ |
| B22 | —SO₂NH₂ | —CF₃ | —Cl |
| B23 | —SO₂NH₂ | —CF₃ | —Br |
| B24 | —SO₂NH₂ | —CF₃ | —I |
| B25 | —SO₂NH₂ | —CF₃ | —F |
| B26 | —SO₂NH₂ | —CH₃ | —OH |
| B27 | —SO₂NH₂ | —Cf₃ | —OH |

TABLE C

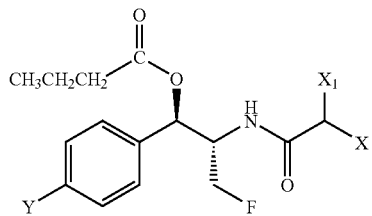

| Compound | Y | X₁ | X |
|---|---|---|---|
| C1 | —SO₂CH₃ | —CH₃ | —CH₃ |
| C2 | —SO₂CH₃ | —CH₃ | —CF₃ |
| C3 | —SO₂CH₃ | —CF₃ | —CF₃ |
| C4 | —SO₂CH₃ | —CF₃ | —Cl |
| C5 | —SO₂CH₃ | —CF₃ | —Br |
| C6 | —SO₂CH₃ | —CF₃ | —I |
| C7 | —SO₂CH₃ | —CF₃ | —F |
| C8 | —SO₂CH₃ | —CH₃ | —OH |
| C9 | —SO₂CH₃ | —CF₃ | —OH |
| C10 | —NO₂ | —CH₃ | —CH₃ |
| C11 | —NO₂ | —CH₃ | —CF₃ |
| C12 | —NO₂ | —CF₃ | —CF₃ |
| C13 | —NO₂ | —CF₃ | —Cl |
| C14 | —NO₂ | —CF₃ | —Br |
| C15 | —NO₂ | —CF₃ | —I |
| C16 | —NO₂ | —CF₃ | —F |
| C17 | —NO₂ | —CH₃ | —OH |
| C18 | —NO₂ | —CF₃ | —OH |
| C19 | —SO₂NH₂ | —CH₃ | —CH₃ |
| C20 | —SO₂NH₂ | —CH₃ | —CF₃ |
| C21 | —SO₂NH₂ | —CF₃ | —CF₃ |
| C22 | —SO₂NH₂ | —CF₃ | —Cl |
| C23 | —SO₂NH₂ | —CF₃ | —Br |
| C24 | —SO₂NH₂ | —CF₃ | —I |
| C25 | —SO₂NH₂ | —CF₃ | —F |
| C26 | —SO₂NH₂ | —CF₃ | —OH |
| C27 | —SO₂NH₂ | —CH₃ | —OH |

TABLE D

| Compound | Y | X₁ | X |
|---|---|---|---|
| D1 | —SO₂CH₃ | —CH₃ | —CH₃ |
| D2 | —SO₂CH₃ | —CH₃ | —CF₃ |
| D3 | —SO₂CH₃ | —CF₃ | —CF₃ |
| D4 | —SO₂CH₃ | —CF₃ | —Cl |
| D5 | —SO₂CH₃ | —CF₃ | —Br |
| D6 | —SO₂CH₃ | —CF₃ | —I |
| D7 | —SO₂CH₃ | —CF₃ | —F |
| D8 | —SO₂CH₃ | —CH₃ | —OH |
| D9 | —SO₂CH₃ | —CF₃ | —OH |
| D10 | —NO₂ | —CH₃ | —CH₃ |
| D11 | —NO₂ | —CH₃ | —CF₃ |
| D12 | —NO₂ | —CF₃ | —CF₃ |
| D13 | —NO₂ | —CF₃ | —Cl |
| D14 | —NO₂ | —CF₃ | —Br |
| D15 | —NO₂ | —CF₃ | —I |
| D16 | —NO₂ | —CF₃ | —F |
| D17 | —NO₂ | —CH₃ | —F |
| D18 | —NO₂ | —CF₃ | —OH |
| D19 | —SO₂NH₂ | —CH₃ | —CH₃ |
| D20 | —SO₂NH₂ | —CH₃ | —CF₃ |
| D21 | —SO₂NH₂ | —CF₃ | —CF₃ |
| D22 | —SO₂NH₂ | —CF₃ | —Cl |
| D23 | —SO₂NH₂ | —CF₃ | —Br |
| D24 | —SO₂NH₂ | —CF₃ | —I |
| D25 | —SO₂NH₂ | —CF₃ | —F |
| D26 | —SO₂NH₂ | —CH₃ | —OH |
| D27 | —SO₂NH₂ | —CF₃ | —OH |

TABLE E

| Compound | Y | X₁ | X |
|---|---|---|---|
| E1 | —SO₂CH₃ | —CH₃ | —CF₃ |
| E2 | —SO₂CH₃ | —CH₃ | —Cl |
| E3 | —SO₂CH₃ | —CH₃ | —Br |
| E4 | —SO₂CH₃ | —CH₃ | —I |
| E5 | —SO₂CH₃ | —CH₃ | —F |
| E6 | —SO₂CH₃ | —CF₃ | —Cl |
| E7 | —SO₂CH₃ | —CF₃ | —Br |
| E8 | —SO₂CH₃ | —CF₃ | —I |
| E9 | —SO₂CH₃ | —CF₃ | —F |
| E10 | —SO₂CH₃ | —CH₃ | —OH |
| E11 | —SO₂CH₃ | —CF₃ | —OH |
| E12 | —NO₂ | —CH₃ | —CF₃ |
| E13 | —NO₂ | —CH₃ | —Cl |
| E14 | —NO₂ | —CH₃ | —Br |
| E15 | —NO₂ | —CH₃ | —I |
| E16 | —NO₂ | —CH₃ | —F |
| E17 | —NO₂ | —CF₃ | —Cl |
| E18 | —NO₂ | —CF₃ | —Br |
| E19 | —NO₂ | —CF₃ | —I |
| E20 | —NO₂ | —CF₃ | —F |
| E21 | —NO₂ | —CH₃ | —OH |
| E22 | —NO₂ | —CF₃ | —OH |
| E23 | —SO₂NH₂ | —CH₃ | —CF₃ |
| E24 | —SO₂NH₂ | —CH₃ | —Cl |
| E25 | —SO₂NH₂ | —CH₃ | —Br |
| E26 | —SO₂NH₂ | —CH₃ | —I |
| E27 | —SO₂NH₂ | —CH₃ | —F |
| E28 | —SO₂NH₂ | —CF₃ | —Cl |
| E29 | —SO₂NH₂ | —CF₃ | —Br |
| E30 | —SO₂NH₂ | —CF₃ | —I |
| E31 | —SO₂NH₂ | —CF₃ | —F |
| E32 | —SO₂NH₂ | —CH₃ | —OH |

TABLE F

| Compound | Y | X₁ | X |
|---|---|---|---|
| F1 | —SO₂CH₃ | —CH₃ | —CF₃ |
| F2 | —SO₂CH₃ | —CH₃ | —Cl |
| F3 | —SO₂CH₃ | —CH₃ | —Br |
| F4 | —SO₂CH₃ | —CH₃ | —I |
| F5 | —SO₂CH₃ | —CH₃ | —F |
| F6 | —SO₂CH₃ | —CF₃ | —Cl |
| F7 | —SO₂CH₃ | —CF₃ | —Br |
| F8 | —SO₂CH₃ | —CF₃ | —I |
| F9 | —SO₂CH₃ | —CF₃ | —F |
| F10 | —SO₂CH₃ | —CH₃ | —OH |
| F11 | —SO₂CH₃ | —CF₃ | —OH |
| F12 | —NO₂ | —CH₃ | —CF₃ |
| F13 | —NO₂ | —CH₃ | —Cl |
| F14 | —NO₂ | —CH₃ | —Br |
| F15 | —NO₂ | —CH₃ | —I |
| F16 | —NO₂ | —CH₃ | —F |
| F17 | —NO₂ | —CF₃ | —Cl |
| F18 | —NO₂ | —CF₃ | —Br |
| F19 | —NO₂ | —CF₃ | —I |
| F20 | —NO₂ | —CF₃ | —F |
| F21 | —NO₂ | —CH₃ | —OH |
| F22 | —NO₂ | —CF₃ | —OH |
| F23 | —SO₂NH₂ | —CH₃ | —CF₃ |
| F24 | —SO₂NH₂ | —CH₃ | —Cl |
| F25 | —SO₂NH₂ | —CH₃ | —Br |
| F26 | —SO₂NH₂ | —CH₃ | —I |
| F27 | —SO₂NH₂ | —CH₃ | —F |
| F28 | —SO₂NH₂ | —CF₃ | —Cl |
| F29 | —SO₂NH₂ | —CF₃ | —Br |
| F30 | —SO₂NH₂ | —CF₃ | —I |
| F31 | —SO₂NH₂ | —CF₃ | —F |
| F32 | —SO₂NH₂ | —CH₃ | —OH |
| F33 | —SO₂NH₂ | —CF₃ | —OH |

TABLE G

| Compound | Y | X₁ | X |
|---|---|---|---|
| G1 | —SO₂CH₃ | —CH₃ | —CF₃ |
| G2 | —SO₂CH₃ | —CH₃ | —Cl |
| G3 | —SO₂CH₃ | —CH₃ | —Br |
| G4 | —SO₂CH₃ | —CH₃ | —I |
| G5 | —SO₂CH₃ | —CH₃ | —F |
| G6 | —SO₂CH₃ | —CF₃ | —Cl |
| G7 | —SO₂CH₃ | —CF₃ | —Br |
| G8 | —SO₂CH₃ | —CF₃ | —I |
| G9 | —SO₂CH₃ | —CF₃ | —F |
| G10 | —SO₂CH₃ | —CH₃ | —OH |
| G11 | —SO₂CH₃ | —CF₃ | —OH |
| G12 | —NO₂ | —CH₃ | —CF₃ |
| G13 | —NO₂ | —CH₃ | —Cl |
| G14 | —NO₂ | —CH₃ | —Br |
| G15 | —NO₂ | —CH₃ | —I |
| G16 | —NO₂ | —CH₃ | —F |
| G17 | —NO₂ | —CF₃ | —Cl |
| G18 | —NO₂ | —CF₃ | —Br |
| G19 | —NO₂ | —CF₃ | —I |
| G20 | —NO₂ | —CF₃ | —F |
| G21 | —NO₂ | —CH₃ | —OH |
| G22 | —NO₂ | —CF₃ | —OH |
| G23 | —SO₂NH₂ | —CH₃ | —CF₃ |
| G24 | —SO₂NH₂ | —CH₃ | —Cl |
| G25 | —SO₂NH₂ | —CH₃ | —Br |
| G26 | —SO₂NH₂ | —CH₃ | —I |
| G27 | —SO₂NH₂ | —CH₃ | —F |
| G28 | —SO₂NH₂ | —CF₃ | —Cl |
| G29 | —SO₂NH₂ | —CF₃ | —Br |
| G30 | —SO₂NH₂ | —CF₃ | —I |
| G31 | —SO₂NH₂ | —CF₃ | —F |

TABLE G-continued

Structure: 4-Y-phenyl with CH₃CH₂CH₂-C(=O)-O- at benzylic position, CH₂F, NH-C(=O)-CHX X₁

| Compound | Y | X₁ | X |
|---|---|---|---|
| G32 | —SO₂NH₂ | —CH₃ | —OH |
| G33 | —SO₂NH₂ | —CF₃ | —OH |

TABLE H

Structure: 4-Y-phenyl with CH₃(CH₂)₄-C(=O)-O- at benzylic position, CH₂F, NH-C(=O)-CHX X₁

| Compound | Y | X₁ | X |
|---|---|---|---|
| H1 | —SO₂CH₃ | —CH₃ | —CF₃ |
| H2 | —SO₂CH₃ | —CH₃ | —Cl |
| H3 | —SO₂CH₃ | —CH₃ | —Br |
| H4 | —SO₂CH₃ | —CH₃ | —I |
| H5 | —SO₂CH₃ | —CH₃ | —F |
| H6 | —SO₂CH₃ | —CF₃ | —Cl |
| H7 | —SO₂CH₃ | —CF₃ | —Br |
| H8 | —SO₂CH₃ | —CF₃ | —I |
| H9 | —SO₂CH₃ | —CF₃ | —F |
| H10 | —SO₂CH₃ | —CH₃ | —OH |
| H11 | —SO₂CH₃ | —CF₃ | —OH |
| H12 | —NO₂ | —CH₃ | —CF₃ |
| H13 | —NO₂ | —CH₃ | —Cl |
| H14 | —NO₂ | —CH₃ | —Br |
| H15 | —NO₂ | —CH₃ | —I |
| H16 | —NO₂ | —CH₃ | —F |
| H17 | —NO₂ | —CF₃ | —Cl |
| H18 | —NO₂ | —CF₃ | —Br |
| H19 | —NO₂ | —CF₃ | —I |
| H20 | —NO₂ | —CF₃ | —F |
| H21 | —NO₂ | —CH₃ | —OH |
| H22 | —NO₂ | —CF₃ | —OH |
| H23 | —SO₂NH₂ | —CH₃ | —CF₃ |
| H24 | —SO₂NH₂ | —CH₃ | —Cl |
| H25 | —SO₂NH₂ | —CH₃ | —Br |
| H26 | —SO₂NH₂ | —CH₃ | —I |
| H27 | —SO₂NH₂ | —CH₃ | —F |
| H28 | —SO₂NH₂ | —CF₃ | —Cl |
| H29 | —SO₂NH₂ | —CF₃ | —Br |
| H30 | —SO₂NH₂ | —CF₃ | —I |
| H31 | —SO₂NH₂ | —CF₃ | —F |
| H32 | —SO₂NH₂ | —CH₃ | —OH |
| H33 | —SO₂NH₂ | —CF₃ | —OH |

TABLE I

Structure: 4-Y-phenyl with OH at benzylic position, CH₂F, NH-C(=O)-CHX X₁

| Compound | Y | X₁ | X |
|---|---|---|---|
| I1 | —SO₂CH₃ | —CH₃ | —CF₃ |
| I2 | —SO₂CH₃ | —CH₃ | —Cl |
| I3 | —SO₂CH₃ | —CH₃ | —Br |
| I4 | —SO₂CH₃ | —CH₃ | —I |
| I5 | —SO₂CH₃ | —CH₃ | —F |
| I6 | —SO₂CH₃ | —CF₃ | —Cl |
| I7 | —SO₂CH₃ | —CF₃ | —Br |
| I8 | —SO₂CH₃ | —CF₃ | —I |
| I9 | —SO₂CH₃ | —CF₃ | —F |
| I10 | —SO₂CH₃ | —CH₃ | —OH |
| I11 | —SO₂CH₃ | —CF₃ | —OH |
| I12 | —NO₂ | —CH₃ | —CF₃ |
| I13 | —NO₂ | —CH₃ | —Cl |
| I14 | —NO₂ | —CH₃ | —Br |
| I15 | —NO₂ | —CH₃ | —I |
| I16 | —NO₂ | —CH₃ | —F |
| I17 | —NO₂ | —CF₃ | —Cl |
| I18 | —NO₂ | —CF₃ | —Br |
| I19 | —NO₂ | —CF₃ | —I |
| I20 | —NO₂ | —CF₃ | —F |
| I21 | —NO₂ | —CH₃ | —OH |
| I22 | —NO₂ | —CF₃ | —OH |
| I23 | —SO₂NH₂ | —CH₃ | —CF₃ |
| I24 | —SO₂NH₂ | —CH₃ | —Cl |
| I25 | —SO₂NH₂ | —CH₃ | —Br |
| I26 | —SO₂NH₂ | —CH₃ | —I |
| I27 | —SO₂NH₂ | —CH₃ | —F |
| I28 | —SO₂NH₂ | —CF₃ | —Cl |
| I29 | —SO₂NH₂ | —CF₃ | —Br |
| I30 | —SO₂NH₂ | —CF₃ | —I |
| I31 | —SO₂NH₂ | —CF₃ | —F |
| I32 | —SO₂NH₂ | —CH₃ | —OH |
| I33 | —SO₂NH₂ | —CF₃ | —OH |

TABLE J

Structure: 4-Y-phenyl with H₃C-C(=O)-O- at benzylic position, CH₂F, NH-C(=O)-CHX X₁

| Compound | Y | X₁ | X |
|---|---|---|---|
| J1 | —SO₂CH₃ | —CH₃ | —CF₃ |
| J2 | —SO₂CH₃ | —CH₃ | —Cl |
| J3 | —SO₂CH₃ | —CH₃ | —Br |
| J4 | —SO₂CH₃ | —CH₃ | —I |
| J5 | —SO₂CH₃ | —CH₃ | —F |
| J6 | —SO₂CH₃ | —CF₃ | —Cl |
| J7 | —SO₂CH₃ | —CF₃ | —Br |
| J8 | —SO₂CH₃ | —CF₃ | —I |
| J9 | —SO₂CH₃ | —CF₃ | —F |
| J10 | —SO₂CH₃ | —CH₃ | —OH |
| J11 | —SO₂CH₃ | —CF₃ | —OH |
| J12 | —NO₂ | —CH₃ | —CF₃ |
| J13 | —NO₂ | —CH₃ | —Cl |
| J14 | —NO₂ | —CH₃ | —Br |
| J15 | —NO₂ | —CH₃ | —I |
| J16 | —NO₂ | —CH₃ | —F |
| J17 | —NO₂ | —CF₃ | —Cl |

TABLE J-continued

[Structure: 4-Y-phenyl with acetate ester, CH2F, and NHC(O)CHX1X amide]

| Compound | Y | X1 | X |
|---|---|---|---|
| J18 | —NO2 | —CF3 | —Br |
| J19 | —NO2 | —CF3 | —I |
| J20 | —NO2 | —CF3 | —F |
| J21 | —NO2 | —CH3 | —OH |
| J22 | —NO2 | —CF3 | —OH |
| J23 | —SO2NH2 | —CH3 | —CF3 |
| J24 | —SO2NH2 | —CH3 | —Cl |
| J25 | —SO2NH2 | —CH3 | —Br |
| J26 | —SO2NH2 | —CH3 | —I |
| J27 | —SO2NH2 | —CH3 | —F |
| J28 | —SO2NH2 | —CF3 | —Cl |
| J29 | —SO2NH2 | —CF3 | —Br |
| J30 | —SO2NH2 | —CF3 | —I |
| J31 | —SO2NH2 | —CF3 | —F |
| J32 | —SO2NH2 | —CH3 | —OH |
| J33 | —SO2NH2 | —CF3 | —OH |

TABLE K

[Structure: 4-Y-phenyl with propanoate ester (CH3CH2C(O)O-), CH2F, and NHC(O)CHX1X amide]

| Compound | Y | X1 | X |
|---|---|---|---|
| K1 | —SO2CH3 | —CH3 | —CF3 |
| K2 | —SO2CH3 | —CH3 | —Cl |
| K3 | —SO2CH3 | —CH3 | —Br |
| K4 | —SO2CH3 | —CH3 | —I |
| K5 | —SO2CH3 | —CH3 | —F |
| K6 | —SO2CH3 | —CF3 | —Cl |
| K7 | —SO2CH3 | —CF3 | —Br |
| K8 | —SO2CH3 | —CF3 | —I |
| K9 | —SO2CH3 | —CF3 | —F |
| K10 | —SO2CH3 | —CH3 | —OH |
| K11 | —SO2CH3 | —CF3 | —OH |
| K12 | —NO2 | —CH3 | —CF3 |
| K13 | —NO2 | —CH3 | —Cl |
| K14 | —NO2 | —CH3 | —Br |
| K15 | —NO2 | —CH3 | —I |
| K16 | —NO2 | —CH3 | —F |
| K17 | —NO2 | —CF3 | —Cl |
| K18 | —NO2 | —CF3 | —Br |
| K19 | —NO2 | —CF3 | —I |
| K20 | —NO2 | —CF3 | —F |
| K21 | —NO2 | —CH3 | —OH |
| K22 | —NO2 | —CF3 | —OH |
| K23 | —SO2NH2 | —CH3 | —CF3 |
| K24 | —SO2NH2 | —CH3 | —Cl |
| K25 | —SO2NH2 | —CH3 | —Br |
| K26 | —SO2NH2 | —CH3 | —I |
| K27 | —SO2NH2 | —CH3 | —F |
| K28 | —SO2NH2 | —CF3 | —Cl |
| K29 | —SO2NH2 | —CF3 | —Br |
| K30 | —SO2NH2 | —CF3 | —I |
| K31 | —SO2NH2 | —CF3 | —F |

TABLE K-continued

[Structure: 4-Y-phenyl with propanoate ester (CH3CH2C(O)O-), CH2F, and NHC(O)CHX1X amide]

| Compound | Y | X1 | X |
|---|---|---|---|
| K32 | —SO2NH2 | —CH3 | —OH |
| K33 | —SO2NH2 | —CF3 | —OH |

TABLE L

[Structure: 4-Y-phenyl with pentanoate ester (CH3(CH2)4C(O)O-), CH2F, and NHC(O)CHX1X amide]

| Compound | Y | X1 | X |
|---|---|---|---|
| L1 | —SO2CH3 | —CH3 | —CF3 |
| L2 | —SO2CH3 | —CH3 | —Cl |
| L3 | —SO2CH3 | —CH3 | —Br |
| L4 | —SO2CH3 | —CH3 | —I |
| L5 | —SO2CH3 | —CH3 | —F |
| L6 | —SO2CH3 | —CF3 | —Cl |
| L7 | —SO2CH3 | —CF3 | —Br |
| L8 | —SO2CH3 | —CF3 | —I |
| L9 | —SO2CH3 | —CF3 | —F |
| L10 | —SO2CH3 | —CH3 | —OH |
| L11 | —SO2CH3 | —CF3 | —OH |
| L12 | —NO2 | —CH3 | —CF3 |
| L13 | —NO2 | —CH3 | —Cl |
| L14 | —NO2 | —CH3 | —Br |
| L15 | —NO2 | —CH3 | —I |
| L16 | —NO2 | —CH3 | —F |
| L17 | —NO2 | —CF3 | —Cl |
| L18 | —NO2 | —CF3 | —Br |
| L19 | —NO2 | —CF3 | —I |
| L20 | —NO2 | —CF3 | —F |
| L21 | —NO2 | —CH3 | —OH |
| L22 | —NO2 | —CF3 | —OH |
| L23 | —SO2NH2 | —CH3 | —CF3 |
| L24 | —SO2NH2 | —CH3 | —Cl |
| L25 | —SO2NH2 | —CH3 | —Br |
| L26 | —SO2NH2 | —CH3 | —I |
| L27 | —SO2NH2 | —CH3 | —F |
| L28 | —SO2NH2 | —CF3 | —Cl |
| L29 | —SO2NH2 | —CF3 | —Br |
| L30 | —SO2NH2 | —CF3 | —I |
| L31 | —SO2NH2 | —CF3 | —F |
| L32 | —SO2NH2 | —CH3 | —OH |
| L33 | —SO2NH2 | —CF3 | —OH |

5.5 Definitions

As used herein, the following terms have the following meaning:

"$C_1$ to $C_3$ hydrocarbon group" means a straight or branched, saturated or unsaturated, non-cyclic hydrocarbon having from 1 to 3 carbon atoms. Representative $C_1$-$C_3$ hydrocarbon groups include, but are not limited to, —$CH_3$, —$CH_2CH_3$, —$CH_2CH_2CH_3$, —$CH(CH_3)_2$, —$CH=CH_2$, —$CH=CH$—$CH_3$, and —$CH_2CH=CH_2$.

"$C_1$-$C_{18}$ hydrocarbon group" means a straight or branched, saturated or unsaturated, cyclic or non-cyclic, aromatic or non-aromatic hydrocarbon having from 1 to 18 carbon atoms. Accordingly, the phrase "an acyl group of formula —C(O)—$R_2$, wherein $R_2$ is a $C_1$ to $C_{18}$ hydrocarbon group that may optionally be substituted with a —$NH_2$ or —COOH" means $R_2$ of the acyl group of formula —C(O)—$R_2$ is a straight or branched, saturated or unsaturated, cyclic or non-cyclic, aromatic or non-aromatic hydrocarbon having from 1 to 18 carbon atoms that may optionally be substituted with a —$NH_2$ or —COOH. Representative acyl group of formula —C(O)—$R_2$, wherein $R_2$ is an unsubstituted $C_1$ to $C_{18}$ hydrocarbon group include, but are not limited to, acetyl, propionyl, butanoyl, hexanoyl, caproyl, laurolyl, myristoyl, palmitoyl, stearoyl, palmioleoyl, oleoyl, linoleoyl, linolenoyl, and benzoyl. Representative acyl groups of formula —C(O)—$R_2$, wherein $R_2$ is a $C_1$ to $C_{18}$ hydrocarbon group that is substituted with a —COOH, include but are not limited to, oxaloyl, malonoyl, succinoyl, glutamoyl, adipoyl, and pimeloyl. Representative acyl groups of formula —C(O)—$R_2$, wherein $R_2$ is a $C_1$ to $C_{18}$ hydrocarbon group that is substituted with a —$NH_2$, include but are not limited to, acyl groups derived from amino acids such as tyrosine, alanine, threonine, serine, hydroxyproline, proline, phenylalanine, leucine, valine, and glycine.

The term "animal" includes, but is not limited to, cow, horse, sheep, pig, ungulate, chimpanzee, monkey, baboon, chicken, turkey, mouse, rabbit, rat, guinea pig, and human.

The term "halo" or "halogen" means —Cl, —Br, —I, or —F.

The phrase "effective amount" when used in connection with a Fenicol Compound means an amount for treating or preventing a bacterial infection.

The phrase "effective amount" when used in connection with another therapeutic agent means an amount for providing the therapeutic effect of the therapeutic agent.

The phrase "treating," "treatment of," and the like includes the amelioration or cessation of a specified condition, typically a bacterial infection.

The phrase "preventing," "prevention of," and the like include the avoidance of the onset of a condition, typically a bacterial infection.

The phrase "substantially free of the enantiomeric stereochemical configuration," means a functional group having a chiral center, and therefore capable of existing in either of two stereochemical configurations, is present in predominately one desired stereochemical configuration, i.e., either the the (R) configuration or the (S) configuration, and greater than 50 percent of the functional groups have the desired stereochemical configuration, preferably at least 75 percent of the functional groups have the desired stereochemical configuration, more preferably at least 90 percent of the functional groups have the desired stereochemical configuration, even more preferably at least 95 percent of the functional groups have the desired stereochemical configuration, and most preferably at least 99 percent of the functional groups have the desired stereochemical configuration. For example the phrase "the (R) stereochemical configuration substantially free of the enantiomeric stereochemical configuration" or the phrase "the (R) stereochemical configuration substantially free of the (S) stereochemical configuration" means a chiral functional group that is predominately present in the (R) stereochemical configuration and that greater than 50 percent of the functional groups have the (R) stereochemical configuration, preferably at least 75 percent of the functional groups have the (R) stereochemical configuration, more preferably at least 90 percent of the functional groups have the (R) stereochemical configuration, even more preferably at least 95 percent of the functional groups have the (R) stereochemical configuration, and most preferably at least 99 percent of the functional groups have the (R) stereochemical configuration.

The phrase "pharmaceutically acceptable salt," as used herein, is a salt formed from an acid and a basic nitrogen group of one of the Fenicol Compounds. Illustrative salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a Fenicol Compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The phrase "THF," as used herein means tetrahydrofuran.

The phrase "DCM," as used herein means dichloromethane.

The phrase "DMF," as used herein means dimethylformamide.

The phrase "EDC" as used herein means ethyl diisopropylcarbodimide.

The phrase "HOBT" as used herein means hydroxybenzotriazole.

The phrase "BOP" as used herein means butyloxyphosphine.

The phrase "DCC" as used herein means dicyclohexylcarbodimide.

5.6 Methods for Making the Fenicol Compounds

5.6.1 Fenicol Compounds of Formula (I), (Ia) and (II)

The Fenicol Compounds of formula (I), (Ia), and (II) can be obtained by the following illustrative method shown below in Scheme 1:

Scheme 1

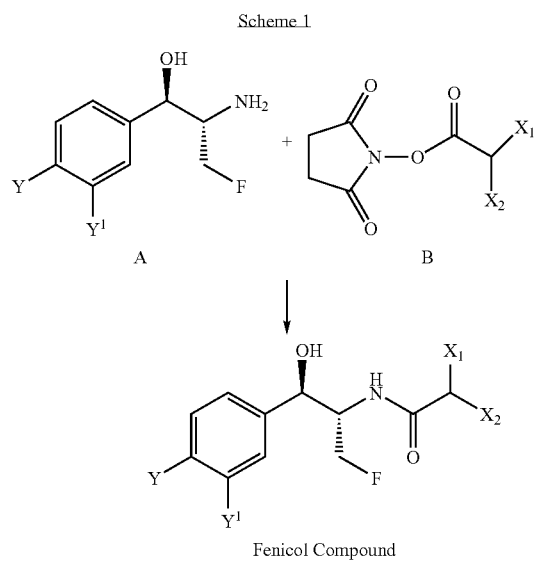

Fenicol Compound

A N-hydroxysuccinimide ester of a carboxylic acid, B, is prepared by methods well known to those of ordinary skill in the art. For example, N-hydroxysuccinimide esters of a carboxylic acid can be obtained by dissolving about 1 eq. of carboxylic acid and 1 eq. of N-hydroxysuccinimide in about 200 mL of an organic solvent, and cooling the resulting solution to about 0° C. About 1 eq. of DCC in 50 mL of the same organic solvent is then added dropwise to the cooled solution of carboxylic acid and N-hydroxysuccinimide. The resulting mixture is allowed to stir for about 30 min. to provide an organic solution of the N-hydroxysuccinimide ester of a carboxylic acid, B, The N-hydroxysuccinimide ester of a carboxylic acid, B, can be recovered by removing the organic solvent under reduced pressure. Preferably, however, the organic solution of the N-hydroxysuccinimide ester of a carboxylic acid, B, is combined directly with the D-(threo)-1-aryl-2-amino-3-fluoro-1-propanol of formula A, as described below. The organic solution of the N-hydroxysuccinimide ester can be stored overnight at refrigerator temperature. Useful solvents for obtaining the N-hydroxysuccinimide ester of a carboxylic acid, B, include, but are not limited to THF, DCM, carbon tetrachloride, chloroform, dioxane, and DMF.

The D-(threo)-1-aryl-2-amino-3-fluoro-1-propanols of formula A are commercially available or can be obtained as described in U.S. Pat. Nos. 4,235,892; 4,311,857; 4,582,918; 4,973,750; 4,876,352; 5,227,494; 4,743,700; 5,567,844; 5,105,009; 5,382,673; 5,352,832; 5,663,361; and WO 03/077828, the contents of which are expressly incorporated herein. For example, D-(threo)-1-p-methylsulfonyl-2-amino-3-fluoro-1-propanol can be easily obtained by hydrolyzing fluorfenicol under acidic conditions.

A D-(threo)-1-aryl-2-amino-3-fluoro-1-propanol, A, (1 eq.) is then reacted with an N-hydroxysuccinimide ester of a carboxylic acid, B, according to methods well known to those skilled in the art to provide the Fenicol Compound of formula (I), (Ia), or (II). Typically, the D-(threo)-1-aryl-2-amino-3-fluoro-1-propanol, A, (1 eq.) is dissolved in about 110 mL of an organic solvent, cooled to about 0° C. and about 1 eq. of the N-hydroxysuccinimide ester of a carboxylic acid, B, dissolved in about 250 mL of the same organic solvent (obtained as described above) is added dropwise and the resulting solution allowed to stir for about 4 h. To the resulting solution is then added about 50 mL of water and the organic solvent removed under reduced pressure. The resulting aqueous mixture is then extracted with an organic solvent, typically DCM. The DCM is washed with aq. 5% sodium carbonate, brine, and water; dried ($Na_2SO_4$); and the solvent removed under reduced pressure to provide the Fenicol Compound of formula (I), (Ia), or (II), which can be purified by recrystallization. Suitable organic solvents for obtaining the Fenicol Compound of formula (I), (Ia), and (II) include, but are not limited to THF, DCM, carbon tetrachloride, chloroform, dioxane, and DMF.

The Fenicol Compounds of formula (I), (Ia), and (II) can also be obtained by reacting a D-(threo)-1-aryl-2-amino-3-fluoro-1-propanol, A, (1 eq.) with an acid anhydride. For example, a D-(threo)-1-aryl-2-amino-3-fluoro-1-propanol, A, (0.1 mmol, 1 eq.) is dissolved in 2.5 mL of an organic solvent and the acid anhydride (at least 1 eq., preferably at least 2 eq., more preferably about 5 eq.) is added dropwisw with stirring to provide a mixture, optionally the acid anhydride can be added as a solution in the same organic solvent (about 1 to 1.5 mL). Additional, organic solvent (about 1.5 mL) is added and the resulting mixture allowed to stir for about 30 min. Additional organic solvent (about 25 mL) is added followed by water (about 20 mL) and the organic layer is separated. The organic layer is then washed 5% sodium carbonate, brine, and water; dried ($Na_2SO_4$); and the solvent removed under reduced pressure to provide the Fenicol Compound of formula (I), (Ia), or (II), which can be purified by recrystallization. Suitable organic solvents for obtaining the Fenicol Compound of formula (I), (Ia), and (II) include, but are not limited to THF, DCM, carbon tetrachloride, chloroform, dioxane, and DMF. Acid anhydrides are commercially available or can be obtained by methods well known to those of ordinary skill in the art.

Progress for each reaction can be monitored using any method well known to those skilled in the art including, but not limited to, high pressure liquid chromatography (HPLC), gas chromatography (GC), thin-layer chromatography (TLC), and nuclear magnetic resonance spectroscopy (NMR).

The Fenicol Compounds of formula (I) and (Ia) wherein Z is an acyl group of formula —C(O)—$R_2$, wherein $R_2$ is a $C_1$ to $C_{18}$ hydrocarbon group that may optionally be substituted with a —$NH_2$ or —COOH can be obtained by acylating the alcohol group of a Fenicol Compound of Formula (I), (Ia), or (II) wherein Z is hydrogen using an acid halide of formula T-C(O)—$R_2$, wherein T is a halide, preferably chloride, and $R_2$ is as defined above, using methods well known to those skilled in the art. The Fenicol Compounds of formula (I) and (Ia) wherein Z is an acyl group of formula —C(O)—$R_2$, wherein $R_2$ is a $C_1$ to $C_{18}$ hydrocarbon group that may optionally be substituted with a —$NH_2$ or —COOH, can also be obtained by acylating the alcohol group of a Fenicol Compound of Formula (I), (Ia), or (II) wherein Z is hydrogen with an acid anhydride using methods well known to those of ordinary skill in the art.

Acid halides can be obtained using methods well known to those skilled in the art such as those described in J. March, *Advanced Organic Chemistry, Reaction Mechanisms and Structure*, 4$^{th}$ ed. John Wiley & Sons, NY, 1992, pp. 437-8. For example, acid halides can be prepared by reacting a carboxylic acid with thionyl chloride, bromide, or iodide. Acid chlorides and bromides can also be prepared by reacting a carboxylic acid with phosphorous trichloride or phosphorous tribromide, respectively. Acid chlorides can also be prepared by reacting a carboxylic acid with $Ph_3P$ in carbon tetrachloride. Acid fluorides can be prepared by reacting a carboxylic acid with cyanuric fluoride. Acid anhydrides can also be obtained using methods well known to those skilled in the art such as those described in J. March, *Advanced Organic Chemistry, Reaction Mechanisms and Structure*, 4th ed. John Wiley & Sons, NY, 1992, pp. 400-402.

5.7.2 Fenicol Compounds of Formula (III)

Method I: The Fenicol Compounds of formula (III) can be obtained by same procedure as described above for obtaining the Fenicol Compounds of formula (I), (Ia), and (II) except that the N-hydroxysuccinimide ester of a carboxylic acid, B, is obtained from an optically active carboxylic acid. Optically active carboxylic acids are commercially available or can be obtained by methods well known to those skilled in the art including, but not limited to resolving a racemic mixture of the carboxylic acid using an optically active amine to provide a pair of diasteriomeric salts that can be separated or by esterifying the optically active acid with an optically active alcohol to provide a pair of diasteriomeric esters that can be separated (See, e.g., *Advanced Organic Chemistry, Reactions, Mechanisms, and Structure*, 4th ed, J. March, Wiley-Interscience, NY (1992), 120-125).

Optically active 2-chloropropionic acid and 2-bromopropionic acid are commercially available from Sigma-Aldrich, St. Louis, Mo. (www.sigma-aldrich.com).

Optically active 2-fluoropropionic acid is commercially available from Metrix Corporation of India.

Optically active 2-iodopropionic acid can be obtained by reacting optically active 2-bromopropionic acid with excess iodide ion. Without wishing to be bound by theory it is believed that the iodide ion replaces the bromide of the optically active 2-bromopropionic acid by an $SN_2$ mechanism to provide the optically active 2-iodopropionic acid of inverted configuration.

Optically active 2-chloro-3,3,3,-trifluoropropionic acid can be obtained by reacting optically active 3,3,3-trifluoro lactic acid (commercially available from Sigma-Aldrich, St. Louis, Mo. (www.sigma-aldrich.com)) with thionly chloride using methods well known to those of ordinary skill in the art. For example, about 7 mmol of 3,3,3-trifluoro lactic acid is dissolved in a mixture of about 15 mL DCM and 3 mL THF. The resultant solution is cooled to about 0° C., 7 mmol of thionyl chloride is added with stirring, and the resulting solution is stirred for about 30 min. The solution is allowed to warm to room temperature and about 7 mmol of thionyl chloride is added with stirring and the resulting solution stirred for about 2 h. The resulting optically active acid chloride of 2-chloro-3,3,3,-trifluoropropionic acid can then be used to acylate the D-(threo)-1-aryl-2-amino-3-fluoro-1-propanol of formula A or can be hydrolyzed, using methods well known to those skilled in the art, to provide optically active 2-chloro-3,3,3, -trifluoropropionic acid.

Optically active 2-bromo-3,3,3,-trifluoropropionic acid can be obtained by the same method used to obtain 2-chloro-3,3,3,-trifluoropropionic acid except that optically active 3,3,3-trifluoro lactic acid is reacted with thionyl bromide instead of thionyl chloride.

Optically active 2-iodo-3,3,3,-trifluoropropionic acid can be obtained by the same method used to obtain 2-chloro-3,3, 3,-trifluoropropionic acid except that optically active 3,3,3-trifluoro lactic acid is reacted with thionyl iodide instead of thionyl chloride.

Optically active 2-fluoro-3,3,3,-trifluoropropionic acid is commercially available from Metric Scientific of India.

Optically active 3,3,3-trifluoro-2-methyl propionic acid can be obtained by resolving racemic 3,3,3-trifluoro-2-methyl propionic acid using methods well known to those skilled in the art. 3,3,3-Trifluoro-2-methyl propionic acid can be obtained by hydrogenating 1-trifluoromethyl acrylic acid (commercially available from Sigma-Aldrich, St. Louis, Mo. (www.sigma-aldrich.com)). For example, 14.2 mmol of 1-trifluoromethyl acrylic acid is dissolved in about 25 mL of methanol and about 0.3 g of Pd/C is added to the solution. The resulting solution is then placed under a hydrogen atmosphere for about 19 h. The catalyst is then removed by filtration and the solvent removed under reduced pressure to provide 3,3,3-trifluoro-2-methyl propionic acid.

Optically active 2-hydroxy-propionic acid is commercially available from Sigma-Aldrich, St. Louis, Mo. (www.sigma-aldrich.com).

Optically active 2-hydroxy-3,3,3,-trifluoropropionic acid is commercially available from Sigma-Aldrich, St. Louis, Mo. (www.sigma-aldrich.com).

In one embodiment, the N-hydroxysuccinimide ester of a carboxylic acid is a N-hydroxysuccinimide ester of (R) 2-chloropropionic acid.

In one embodiment, the N-hydroxysuccinimide ester of a carboxylic acid is a N-hydroxysuccinimide ester of (R) 2-bromopropionic acid.

In one embodiment, the N-hydroxysuccinimide ester of a carboxylic acid is a N-hydroxysuccinimide ester of (R)-2-iodopropionic acid.

In one embodiment, the N-hydroxysuccinimide ester of a carboxylic acid is a N-hydroxysuccinimide ester of (R)-2-fluoropropionic acid.

In one embodiment, the N-hydroxysuccinimide ester of a carboxylic acid is a N-hydroxysuccinimide ester (R)-2-hydroxypropionic acid.

In one embodiment, the N-hydroxysuccinimide ester of a carboxylic acid is a N-hydroxysuccinimide ester of (R)-2-chloro-3,3,3,-trifluoropropionic acid.

In one embodiment, the N-hydroxysuccinimide ester of a carboxylic acid is a N-hydroxysuccinimide ester of (R)-2-bromo-3,3,3,-trifluoropropionic acid.

In one embodiment, the N-hydroxysuccinimide ester of a carboxylic acid is a N-hydroxysuccinimide ester of (R)-2-iodo-3,3,3,-trifluoropropionic acid.

In one embodiment, the N-hydroxysuccinimide ester of a carboxylic acid is a N-hydroxysuccinimide ester of (R)-2-fluoro-3,3,3,-trifluoropropionic acid.

In one embodiment, the N-hydroxysuccinimide ester of a carboxylic acid is a N-hydroxysuccinimide ester of (R)-2-hydroxy-3,3,3,-trifluoropropionic acid.

In one embodiment, the N-hydroxysuccinimide ester of a carboxylic acid is a N-hydroxysuccinimide ester of (S) 2-chloropropionic acid.

In one embodiment, the N-hydroxysuccinimide ester of a carboxylic acid is a N-hydroxysuccinimide ester of (S) 2-bromopropionic acid.

In one embodiment, the N-hydroxysuccinimide ester of a carboxylic acid is a N-hydroxysuccinimide ester of (S)-2-iodopropionic acid.

In one embodiment, the N-hydroxysuccinimide ester of a carboxylic acid is a N-hydroxysuccinimide ester of (S)-2-fluoropropionic acid.

In one embodiment, the N-hydroxysuccinimide ester of a carboxylic acid is a N-hydroxysuccinimide ester (S)-2-hydroxypropionic acid.

In one embodiment, the N-hydroxysuccinimide ester of a carboxylic acid is a N-hydroxysuccinimide ester of (S)-2-chloro-3,3,3,-trifluoropropionic acid.

In one embodiment, the N-hydroxysuccinimide ester of a carboxylic acid is a N-hydroxysuccinimide ester of (S)-2-bromo-3,3,3-trifluoropropionic acid.

In one embodiment, the N-hydroxysuccinimide ester of a carboxylic acid is a N-hydroxysuccinimide ester of (S)-2-iodo-3,3,3,-trifluoropropionic acid.

In one embodiment, the N-hydroxysuccinimide ester of a carboxylic acid is a N-hydroxysuccinimide ester of (S)-2-fluoro-3,3,3,-trifluoropropionic acid.

In one embodiment, the N-hydroxysuccinimide ester of a carboxylic acid is a N-hydroxysuccinimide ester of (S)-2-hydroxy-3,3,3,-trifluoropropionic acid.

Method II: The Fenicol Compounds of formula (III) wherein the acylamido group has the (R) stereochemical configuration substantially free of the (S) stereochemical configuration can also be obtained by reacting a D-(threo)-1-aryl-2-amino-3-fluoro-1-propanol, A, with at least about 2 eq., preferably at least about about 3 eq., and more preferably about 3 eq. of a racemic mixture of an N-hydroxysuccinimide ester of a carboxylic acid, B. Unexpectedly, the product is a Fenicol Compounds of formula (III) wherein the acylamido group has the (R) stereochemical configuration substantially free of the (S) stereochemical configuration. Without wishing to be bound by theory, it is believed that the (R)-N-hydroxysuccinimide ester of a carboxylic acid, B, reacts more quickly with D-(threo)-1-aryl-2-amino-3-fluoro-1-propanol than the (S)-N-hydroxysuccinimide ester of a carboxylic acid.

Accordingly, the invention further relates to a method of preparing a Fenicol Compound of formula (III) wherein the acylamido group has the (R) stereochemical configuration substantially free of the (S) stereochemical configuration. The method involves combining a D-(threo)-1-aryl-2-amino-3-fluoro-1-propanol, A, with at least about 2 eq., preferably at least about about 3 eq., and more preferably about 3 eq. of a racemic mixture of a N-hydroxysuccinimide ester of a carboxylic acid, B, for sufficient time to acylate substantially all of the D-(threo)-1-aryl-2-amino-3-fluoro-1-propanol, A, and recovering the Fenicol Compound of formula (III) wherein the acylamido group has the (R) stereochemical configuration substantially free of the (S) stereochemical configuration.

Typical reaction conditions are the same as those described above for reacting a N-hydroxysuccinimide ester of a carboxylic acid, B, with a D-(threo)-1-aryl-2-amino-3-fluoro-1-propanol to provide a Fenicol Compound of formula (I), (Ia), or (II).

In one embodiment, the D-(threo)-1-aryl-2-amino-3-fluoro-1-propanol, A, is combined with about 3 eq. of the racemic mixture of the N-hydroxysuccinimide ester of a carboxylic acid.

In one embodiment, the D-(threo)-1-aryl-2-amino-3-fluoro-1-propanol, A, is D-(threo)-1-p-methylsulfonyl-2-amino-3-fluoro-1-propanol.

In one embodiment, the D-(threo)-1-aryl-2-amino-3-fluoro-1-propanol, A, is D-(threo)-1-p-nitro-2-amino-3-fluoro-1-propanol.

In one embodiment, the racemic mixture of a N-hydroxysuccinimide ester of a carboxylic acid, B, is a N-hydroxysuccinimide ester of racemic 2-chloropropionic acid.

In one embodiment, the racemic mixture of a N-hydroxysuccinimide ester of a carboxylic acid, B, is a N-hydroxysuccinimide ester of racemic 2-bromopropionic acid.

In one embodiment, the racemic mixture of a N-hydroxysuccinimide ester of a carboxylic acid, B, is a N-hydroxysuccinimide ester of racemic 2-iodopropionic acid.

In one embodiment, the racemic mixture of a N-hydroxysuccinimide ester of a carboxylic acid, B, is a N-hydroxysuccinimide ester of racemic 2-fluoropropionic acid.

In one embodiment, the racemic mixture of a N-hydroxysuccinimide ester of a carboxylic acid, B, is a N-hydroxysuccinimide ester of racemic 2-hydroxypropionic acid.

In one embodiment, the racemic mixture of a N-hydroxysuccinimide ester of a carboxylic acid, B, is a N-hydroxysuccinimide ester of racemic 2-chloro-3,3,3,-trifluoropropionic acid.

In one embodiment, the racemic mixture of a N-hydroxysuccinimide ester of a carboxylic acid, B, is a N-hydroxysuccinimide ester of racemic 2-bromo-3,3,3,-trifluoropropionic acid.

In one embodiment, the racemic mixture of a N-hydroxysuccinimide ester of a carboxylic acid, B, is a N-hydroxysuccinimide ester of racemic 2-iodo-3,3,3,-trifluoropropionic acid.

In one embodiment, the racemic mixture of a N-hydroxysuccinimide ester of a carboxylic acid, B, is a N-hydroxysuccinimide ester of racemic 2-fluoro-3,3,3,-trifluoropropionic acid.

In one embodiment, the racemic mixture of a N-hydroxysuccinimide ester of a carboxylic acid, B, is a N-hydroxysuccinimide ester of racemic 2-hydroxy-3,3,3,-trifluoropropionic acid.

In one embodiment, the racemic mixture of a N-hydroxysuccinimide ester of a carboxylic acid, B, is a N-hydroxysuccinimide ester of racemic 3,3,3-trifluoro-2-methyl propionic acid.

In one embodiment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 2-chloropropionic acid.

In one embodiment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 2-bromopropionic acid.

In one embodiment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 2-hydroxypropionic acid.

In one embodiment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 2-chloro-3,3,3,-trifluoropropionic acid.

In one embodiment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 2-bromo-3,3,3,-trifluoropropionic acid. diment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 2-iodopropionic acid.

In one embodiment, the D-(threo)-1-aryl-2-amino-3-fluoro-1-propanol, A, is D-(threo)-1-p-methylsulfonyl-2- amino-3-fluoro-1-propanol and the racemic mixture of a N-hydroxysuccinimide ester of a carboxylic acid, B, is a N-hydroxysuccinimide ester of racemic 2-fluoropropionic acid.

In one embodiment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 2-iodo-3,3,3,-trifluoropropionic acid.

In one embodiment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 2-fluoro-3,3,3,-trifluoropropionic acid.

In one embodiment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 2-hydroxy-3,3,3,-trifluoropropionic acid.

In one embodiment, the D-(threo)-1-aryl-2-amino-3-fluoro-1-propanol, A, is D-(threo)-1-p-methylsulfonyl-2-amino-3-fluoro-1-propanol and the racemic mixture of a N-hydroxysuccinimide ester of a carboxylic acid, B, is a N-hydroxysuccinimide ester of racemic 3,3,3-trifluoro-2-methyl propionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-chloropropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-bromopropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-iodopropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-fluoropropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-hydroxypropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-chloro-3,3,3,-trifluoropropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-bromo-3,3,3,-trifluoropropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-iodo-3,3,3,-trifluoropropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-fluoro-3,3,3,-trifluoropropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 2-hydroxy-3,3,3,-trifluoropropionic acid.

In one embodiment, the D-(threo)-1-aryl-2-amino-3-fluoro-1-propanol, A, is D-(threo)-1-p-nitro-2-amino-3-fluoro-1-propanol and the racemic mixture of a N-hydroxysuccinimide ester of a carboxylic acid, B, is a N-hydroxysuccinimide ester of racemic 3,3,3-trifluoro-2-methyl propionic acid.

Method III: The Fenicol Compounds of formula (III) wherein the acylamido group has the (R) stereochemical configuration substantially free of the (S) stereochemical configuration can also be obtained by reacting a D-(threo)-1-aryl-2-amino-3-fluoro-1-propanol, A, with about 1 eq. of a racemic mixture of an N-hydroxysuccinimide ester, B, to provide Fenicol Compounds of formula (III) wherein the acylamido group is present in both the (R) configuration and the (S) configuration, i.e., the mixture is not substantially free of the Fenicol Compounds of formula (III) wherein the acylamido group is present in the (S) configuration. Fenicol Compound of formula (III) wherein the acylamido group is present in both the (R) configuration and the (S) configuration is then contacted with silica gel. Unexpectedly, the Fenicol Compound of formula (III) wherein the acylamido group is present in the (S) configuration is isomerized to the Fenicol Compound of formula (III) wherein the acylamido group has (R) stereochemical configuration to provide a Fenicol Compound of formula (III) wherein the acylamido group has (R) stereochemical configuration substantially free of the (S) stereochemical configuration. Without wishing to be bound by theory, it is believed that the silica gel catalyzes the isomerization of Fenicol Compound of formula (III) wherein the acylamido group has the (S) configuration to the Fenicol Compound of formula (III) wherein the acylamido group has the (R) stereochemical configuration substantially free of the (S) stereochemical configuration.

Accordingly, the invention further relates to a method of converting a Fenicol Compound of formula (III) wherein the acylamido group has the (S) stereochemical configuration to a Fenicol Compound of formula (III) wherein the acylamido group has the (R) stereochemical configuration. The method involves contacting the Fenicol Compounds of formula (III) wherein the acylamido group has the (S) configuration with silica gel for a sufficient time to convert the Fenicol Compounds of formula (III) wherein the acylamido group has the (S) configuration to a Fenicol Compounds of formula (III) wherein the acylamido group has the (R) stereochemical configuration. In one embodiment, the method converts Fenicol Compound of formula (III) wherein the acylamido group is present in both the (R) stereochemical configuration and the (S) stereochemical configuration to a Fenicol Compound of formula (II) wherein the acylamido group has the (R) stereochemical configuration substantially free of the (S) stereochemical configuration. In one embodiment, the Fenicol Compounds of formula (III) wherein the acylamido group has the (S) configuration is present as part of an equimolar mixture of Fenicol Compounds of formula (III) wherein the acylamido group has the (S) configuration and Fenicol Compounds of formula (III) wherein the acylamido group has the (R) configuration.

In one embodiment, the Fenicol Compound of formula (III) wherein the acylamido group has the (S) configuration is contacted with silica gel for a sufficient time to convert the Fenicol Compound of formula (III) wherein the acylamido group has the (S) configuration to a Fenicol Compound of formula (III) wherein the acylamido group has the (R) stereochemical configuration by dissolving the Fenicol Compound of formula (III) wherein the acylamido group has the (S) configuration in a solvent, adding silica gel, and allowing the resulting mixture to stir for sufficient time to convert the Fenicol Compound of formula (III) wherein the acylamido group has the (S) stereochemical configuration to a Fenicol Compound of formula (III) wherein the acylamido group has the (R) stereochemical configuration.

Typically, the reaction is conducted at a temperature of ranging from about about 25° C. to 100° C. Preferably, the reaction is conducted at the reflux temperature of the solvent.

Suitable solvents include, but are not limited to THF, dioxane, methanol, ethanol, DCM, and chloroform.

Typically, the Fenicol Compound of formula (III) wherein the acylamido group has the (S) configuration is present in an amount of about 0.05 to 1 g per 10 mL of solvent, preferably about 0.1 to 0.5 g per 10 mL of solvent, and more preferably about 0.15 to about 0.3 g per 10 mL of solvent.

Typically, the ratio of silica to Fenicol Compound of formula (III) ranges from about 0.1:1 to 10:1, preferably about 0.5:1 to 2:1, more preferably about 0.3:1 to about 3:1, and most preferably about 0.25:1.

Typically, the mixture is allowed to stir for a time period ranging from about 2 to 24 h and preferably about 3 to 12 h.

In another embodiment, the Fenicol Compound of formula (III) wherein the acylamido group has the (S) configuration is contacted with silica gel by simply placing the Fenicol Compound of formula (III) wherein the acylamido group has the (S) configuration on a silica column and eluting the column with a solvent.

Suitable solvents for eluting the silica column include, but are not limited to THF, dioxane, methanol, ethanol, DCM, and chloroform.

Typically, the amount of the silica used in the column is at least about 10 fold, preferably at least about 20 fold, more preferably at least about 30 fold, and most preferably at least about 40 fold greater than the amount of the Fenicol Compound of formula (III) wherein the acylamido group has the (S) configuration that is applied to the column.

Typically, the silica column is eluted at a rate of about 1 mL/min. or less.

5.7.3 Fenicol Compounds of Formula (IV)

The Fenicol Compounds of formula (IV) can be obtained by same procedure as described above for obtaining the Fenicol Compounds of formula (I), (Ia), and (II).

5.8 Therapeutic Uses of the Fenicol Compounds,

In accordance with the invention, the Fenicol Compounds are administered to an animal in need of treatment or prevention of a bacterial infection. The Fenicol Compounds are a broad spectrum antibacterial useful to treat bacterial infections caused by both gram negative and gram positive bacteria.

Accordingly, the invention further relates to a method of treating a bacterial infection in an animal comprising administering to an animal in need thereof an effective amount of a compound of formula (IV):

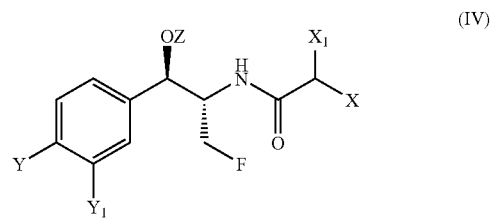

or a pharmaceutically acceptable salt thereof, wherein
X is —CH$_3$ and X$_1$ is —CH$_3$, —CF$_3$, or —OH or
X is —CF$_3$ and X$_1$ is —CF$_3$; -halo, or —OH;
Z is hydrogen or an acyl group of formula —C(O)—R$_2$, wherein R$_2$ is a C$_1$ to C$_{18}$ hydrocarbon group that may optionally be substituted with a —NH$_2$ or —COOH;
Y and Y$^1$ is —H; —NO$_2$; —SO$_2$R$_1$; —SOR$_1$; —SR$_1$; —SONH$_2$; —SO$_2$NH$_2$; —SONHR$_1$; —SO$_2$NHR$_1$; —COR$_2$; —OR$_1$; —R$_1$; —CN, -halo; -phenyl; or -phenyl substituted with -halo, —NO$_2$, —SO$_2$CH$_3$, —R$_1$, or —OR$_1$;
R$_1$ is a C$_1$ to C$_3$ hydrocarbon group; and
halo is —Cl, —Br, —I, or —F.
In one embodiment, Z is —H.
In one embodiment, Z is an acyl group of formula —C(O)—R$_2$, wherein R$_2$ is a C$_1$ to C$_{18}$ hydrocarbon group that may optionally be substituted with a —NH$_2$ or —COOH.
In one embodiment, Z is an acyl group of formula —C(O)—R$_2$, wherein R$_2$ is an unsubstituted C$_1$ to C$_{18}$ hydrocarbon group.
In one embodiment, Z is acetyl.
In one embodiment, Z is butanoyl.
In one embodiment, Z is hexanoyl.
In one embodiment, Y$_1$ is hydrogen.
In one embodiment, Z is hydrogen, Y$_1$ is hydrogen and Y is —NO$_2$, —SO$_2$CH$_3$, or —SONH$_2$.
In one embodiment, Z is hydrogen, Y$_1$ is hydrogen, and Y is —NO$_2$.
In one embodiment, Z is hydrogen, Y$_1$ is hydrogen, and Y is —SO$_2$CH$_3$.
In one embodiment, Z is hydrogen, Y$_1$ is hydrogen, and Y is —SO$_2$NH$_2$.
In one embodiment, Z is hydrogen, X is —CH$_3$, and X$_1$ is —CH$_3$.
In one embodiment, Z is hydrogen, X is —CH$_3$, and X$_1$ is —CF$_3$.
In one embodiment, Z is hydrogen, X is —CH$_3$, and X$_1$ is —OH.
In one embodiment, Z is hydrogen, X is —CF$_3$, and X$_1$ is —CF$_3$.

In one embodiment, Z is hydrogen, X is —$CF_3$, and $X_1$ is -halo.

In one embodiment, Z is hydrogen, X is —$CF_3$, and $X_1$ is —Cl.

In one embodiment, Z is hydrogen, X is —$CF_3$, and $X_1$ is —Br.

In one embodiment, Z is hydrogen, X is —$CF_3$, and $X_1$ is —I.

In one embodiment, Z is hydrogen, X is —$CF_3$, and $X_1$ is —F.

In one embodiment, Z is hydrogen, X is —$CF_3$, and $X_1$ is —OH.

In one embodiment, Z is hydrogen, X is —$CH_3$, $X_1$ is —$CH_3$, $Y_1$ is hydrogen, and Y is —$SO_2CH_3$.

In one embodiment, Z is hydrogen, X is —$CH_3$, $X_1$ is —$CH_3$, $Y_1$ is hydrogen, and Y is —$NO_2$.

In one embodiment, Z is hydrogen, X is —$CH_3$, $X_1$ is —$CH_3$, $Y_1$ is hydrogen, and Y is —$SO_2NH_2$.

In one embodiment, Z is hydrogen, X is —$CH_3$, $X_1$ is —$CF_3$, $Y_1$ is hydrogen, and Y is —$SO_2CH_3$.

In one embodiment, Z is hydrogen, X is —$CH_3$, $X_1$ is —$CF_3$, $Y_1$ is hydrogen, and Y is —$NO_2$.

In one embodiment, Z is hydrogen, X is —$CH_3$, $X_1$ is —$CF_3$, $Y_1$ is hydrogen, and Y is —$SO_2NH_2$.

In one embodiment, Z is hydrogen, X is —$CH_3$, $X_1$ is —OH, $Y_1$ is hydrogen, and Y is —$SO_2CH_3$.

In one embodiment, Z is hydrogen, X is —$CH_3$, $X_1$ is —OH, $Y_1$ is hydrogen, and Y is —$NO_2$.

In one embodiment, Z is hydrogen, X is —$CH_3$, $X_1$ is —OH, $Y_1$ is hydrogen, and Y is —$SO_2NH_2$.

In one embodiment, Z is hydrogen, X is —$CF_3$, $X_1$ is -halo, $Y_1$ is hydrogen, and Y is —$SO_2CH_3$.

In one embodiment, Z is hydrogen, X is —$CF_3$, $X_1$ is -halo, $Y_1$ is hydrogen, and Y is —$NO_2$.

In one embodiment, Z is hydrogen, X is —$CF_3$, $X_1$ is -halo, $Y_1$ is hydrogen, and Y is —$SO_2NH_2$.

In one embodiment, Z is hydrogen, X is —$CF_3$, $X_1$ is —Cl, $Y_1$ is hydrogen, and Y is —$SO_2CH_3$.

In one embodiment, Z is hydrogen, X is —$CF_3$, $X_1$ is —Cl, $Y_1$ is hydrogen, and Y is —$NO_2$.

In one embodiment, Z is hydrogen, X is —$CF_3$, $X_1$ is —Cl, $Y_1$ is hydrogen, and Y is —$SO_2NH_2$.

In one embodiment, Z is hydrogen, X is —$CF_3$, $X_1$ is —Br, $Y_1$ is hydrogen, and Y is —$SO_2CH_3$.

In one embodiment, Z is hydrogen, X is —$CF_3$, $X_1$ is —Br, $Y_1$ is hydrogen, and Y is —$NO_2$.

In one embodiment, Z is hydrogen, X is —$CF_3$, $X_1$ is —Br, $Y_1$ is hydrogen, and Y is —$SO_2NH_2$.

In one embodiment, Z is hydrogen, X is —$CF_3$, $X_1$ is —I, $Y_1$ is hydrogen, and Y is —$SO_2CH_3$.

In one embodiment, Z is hydrogen, X is —$CF_3$, $X_1$ is —I, $Y_1$ is hydrogen, and Y is —$NO_2$.

In one embodiment, Z is hydrogen, X is —$CF_3$, $X_1$ is —I, $Y_1$ is hydrogen, and Y is —$SO_2NH_2$.

In one embodiment, Z is hydrogen, X is —$CF_3$, $X_1$ is —F, $Y_1$ is hydrogen, and Y is —$SO_2CH_3$.

In one embodiment, Z is hydrogen, X is —$CF_3$, $X_1$ is —F, $Y_1$ is hydrogen, and Y is —$NO_2$.

In one embodiment, Z is hydrogen, X is —$CF_3$, $X_1$ is —F, $Y_1$ is hydrogen, and Y is —$SO_2NH_2$.

In one embodiment, Z is hydrogen, X is —$CF_3$, $X_1$ is —OH, $Y_1$ is hydrogen, and Y is —$SO_2CH_3$.

In one embodiment, Z is hydrogen, X is —$CF_3$, $X_1$ is —OH, $Y_1$ is hydrogen, and Y is —$NO_2$.

In one embodiment, Z is hydrogen, X is —$CF_3$, $X_1$ is —OH, $Y_1$ is hydrogen, and Y is —$SO_2NH_2$.

In one embodiment, Z is hydrogen, X is —$CF_3$, $X_1$ is —$CF_3$, $Y_1$ is hydrogen, and Y is —$SO_2CH_3$.

In one embodiment, Z is hydrogen, X is —$CF_3$, $X_1$ is —$CF_3$, $Y_1$ is hydrogen, and Y is —$NO_2$.

In one embodiment, Z is hydrogen, X is —$CF_3$, $X_1$ is —$CF_3$, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, and Y is —$NO_2$, —$SO_2CH_3$, or —$SONH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, and $X_1$ is —$CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, and $X_1$ is —$CF_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, and $X_1$ is —OH.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, and $X_1$ is —$CF_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, and $X_1$ is -halo.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, and $X_1$ is -halo.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, and $X_1$ is —Cl.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, and $X_1$ is —Br.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, and $X_1$ is —I.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, and $X_1$ is —F.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, and $X_1$ is —OH.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, $X_1$ is —$CH_3$, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, $X_1$ is —$CH_3$, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, $X_1$ is —$CH_3$, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, $X_1$ is —OH, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, $X_1$ is —OH, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, $X_1$ is —OH, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, $X_1$ is —$CF_3$, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, $X_1$ is —$CF_3$, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CH_3$, $X_1$ is —$CF_3$, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is -halo, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is -halo, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is -halo, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —Cl, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —Cl, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —Cl, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —Br, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —Br, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —Br, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —I, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —I, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —I, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —F, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —F, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —F, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —OH, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —OH, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —OH, $Y_1$ is hydrogen, and Y is —$SO_2NH_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —$CF_3$, $Y_1$ is hydrogen, and Y is —$SO_2CH_3$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —$CF_3$, $Y_1$ is hydrogen, and Y is —$NO_2$.

In one embodiment, Z is an acyl group of formula —C(O)—$R_2$, wherein $R_2$ is a $C_1$ to $C_{18}$ hydrocarbon group that may optionally be substituted with a —$NH_2$ or —COOH, X is —$CF_3$, $X_1$ is —$CF_3$, $Y_1$ is hydrogen, and Y is —$SO_2NH_2$.

The invention further relates to a method of treating a bacterial infection in an animal comprising administering to an animal in need thereof an effective amount of a compound of formula (I).

The invention further relates to a method of treating a bacterial infection in an animal comprising administering to an animal in need thereof an effective amount of a compound of formula (Ia).

The invention further relates to a method of treating a bacterial infection in an animal comprising administering to an animal in need thereof an effective amount of a compound of formula (II).

The invention further relates to a method of treating a bacterial infection in an animal comprising administering to an animal in need thereof an effective amount of a compound of formula (III).

Representative bacterial infections that can be treated using the Fenicol Compounds of the invention include, but are not limited to, bacterial infections caused by bacteria of the genus *Pasteurella, Haemophilus, Fusobacterium, Moraxella, Bacteroides, Aeromonas, Escherichia, Enterobacter, Klebsiella, Salmonella, Shigella, Serratia, Ureaplasma, Chlamydia, Actinobacillus, Streptococcus, Edwardsiella, Staphylococcus, Enterococcus, Bordetella, Proteus, Mycoplasma,* or *Mannheimia.*

Representative bacterial infections that can be treated using the Fenicol Compounds of the invention include, but are not limited to, bacterial infections caused by *Pasteurella haemolytica, Pasteurella multocida, Pasteurella haemolytica, Haemophilus somnus, Actinobacillus pleuropneumoniae, Actinomyces pyogenes, Pseudomonas aeruginosa, Klebsiella pneumonia, Klebsiella oxytoca, Escherichia faecalis, Escherichia coli, Staphylococcus aureaus, Staphylococcus intermedius, Enterococcus faecalis, Enterococcus faecium, Streptococcus pyogenes, Bacillus subtilis, Peptococcus indolicus, Mycoplasma bovis, Mycoplasma dispar, Mycoplasma hyopneumoniae, Mycoplasma hyorhinis, Mycoplasma gallisepticum, Mycoplasma mycoides, Mycoplasma ovipneumonia, Haemophilus influenzae, Klebsiella salmonella, Shigella, Proteus enterobacter, Enterobacter cloacae, Mannhemia haemolytica, Haemophilus somnus, Fusobacterium necrophorum, Bacterioides melaninogenicus, Proteus mirabillis, Streptococcus suis, Salmonella cholerasuis, Edwardsiella ictaluri, Aeromonas salmonicidia, Actinobacilus pleuropneumoniae,* and *Bordetella bronchoseptica.*

In one embodiment, the bacteria is *Pasteurella haemolytica, Pasteurella multocida,* or *Haemophilus somnus*

In one embodiment, the animal is a human.
In one embodiment, the animal is a dog.
In one embodiment, the animal is a cat.
In one embodiment, the animal is a cow.
In one embodiment, the animal is a pig.
In one embodiment, the animal is a horse.

Typically, the minimum inhibitory concentration of the Fenicol Compound against a specific bacteria is less than 10 μg/mL, preferably less than 5 μg/mL, more preferably less than 1 μg/mL, and most preferably less than 0.5 μg/mL.

The activity of a Fenicol Compound against a bacteria is determined using standard dilution tests. For example, the minimum inhibitory concentrations can be determined using the disk diffusion susceptibility testing method described in *Clinical Microbiology Procedures Handbook*, volume 1, edited by Henry D. Isenberg, American Society for Microbiology, 1992, section 5.1 or the well known method of Bauer et al. "*Antibiotic Susceptibility Testing by a Standardized Single Disc Method*," Amer. J. Clin. Pathol., 45, p. 493-496.

Table I provides the minimum inhibitory concentration (MIC) for illustrative Fenicol Compounds against various bacteria.

TABLE I

| Fenicol Compound | Minimum Inhibitory Concentration (μg/mL)[a] | | | | | | |
|---|---|---|---|---|---|---|---|
| | K. pneumoniae | E. faecalis | E. coli | S. aureus | S. pyogenes | B. subtitis | B. bronchoseptica |
| Fluorfenicol | 3 | 3 | 1 | 1 | 1 | 1 | 1 |
| A1 | | | 5 | 3 | 5 | 2 | |
| A2 | | 5 | 7 | 7 | 5 | 5 | |
| E2 + I2 (Racemic Mixture) | 5 | | 3 | 2 | | 0.5 | 3 |
| E2 | 5 | >5 | 3 | 3 | >5 | 1 | >5 |
| I2 | 3 | 2 | 0.5 | 5 | 3 | 5 | 5 |
| E5 + I5 (Racemic Mixture) | 5 | 3 | 5 | 5 | 5 | 1 | >10 |
| D-threo-2-chloro-N-[1-(fluoromethyl)-2-hydroxy-2-[4-methylsulfonyl)phenyl]ethyl]-acetamide | 5 | | 3 | 2 | | 0.5 | 3 |

[a]Minimum Inhibitory Concentrations were determined using the disk diffusion susceptibility testing method described in Clinical Microbiology Procedures Handbook, volume 1, edited by Henry D. Isenberg, American Society for Microbiology, 1992, section 5.1.

The results reported in Table I show that the Fenicol Compounds are effective antibiotics and therefore are useful for treating or preventing bacterial infections in animals.

The Fenicol Compounds have lower clearance rates than conventional antibiotics, such as fluorfenicol (commercially available as NUFLOR®). Conventional antibiotics, such as fenicol, are ineffective in many animals because the clearance rate of the antibiotic is so rapid that it is excreted by the animal before it can exert its antibacterial effect. For example, fluorfenicol (commercially available as NUFLOR®), when subcutaneously administered to dogs is cleared too rapidly to be effective. Accordingly, the Fenicol Compounds are particularly useful for treating bacterial infections in animals where these conventional antibiotics are ineffective because of rapid clearance.

FIG. 1 shows the serum plasma levels for NUFLOR® and Fenicol Compound A1 administered subcutaneously to dogs at a dose of 40 mg/kg as a function of time. NUFLOR® was commercially available from Schering-Plough Animal Health, New Jersey. Fenicol Compound A1 was formulated as a solution containing 3 mg of Fenicol Compound A1, 9 g N-methyl pyrrolidone, 2.25 g propylene glycol, QS to 20 mL with polyethylene glycol. FIG. 1 clearly shows that the clearance rate for NUFLOR® in dogs is rapid. Indeed, the clearance rate of NUFLOR® in dogs is so rapid that NUFLOR® only attains a maximum serum concentration of less than 0.8 μg/mL. As a result of this rapid clearance, NUFLOR® is ineffective as an antibiotic in dogs. In contrast, Fenicol Compound A1 is cleared much more slowly in dogs such that Fenicol Compound A1 achieves a maximum serum level of almost 7 μg/mL. Accordingly, Fenicol Compound A1 can be more effective at treating or preventing bacterial infections in dogs than NUFLOR®.

Similarly, the clearance rate of Fenicol compound A2 in dogs is much slower than the clearance rate of NUFLOR®. Therefore, administering Fenicol Compound A2 to dogs results in higher serum concentrations of the antibiotic than are obtainable when NUFLOR® is administered to dogs. FIG. 2 shows the serum concentration of Fenicol Compound A2 when Fenicol Compound A2 was administered to dogs as a 40 mg/kg subcutaneous injection of a formulation containing 925 mg of Fenicol Compound A2, 2 mL N-methylpyrrolidone, 0.5 mL propylene glycol, QS to 5 mL with polyethylene glycol. FIG. 2 clearly shows that Fenicol Compound A2, when administered to dogs, achieves a maximum serum concentration of almost 5 μg/mL. Accordingly, Fenicol Compound A2 can be more effective at treating or preventing bacterial infections in dogs than NUFLOR®.

Similarly, it was observed that a Fenicol Compound of formula (V)

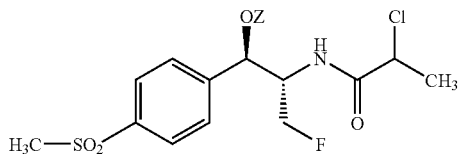

wherein Z is a hydrogen or an acyl group of formula —C(O)—$R_2$, wherein $R_2$ is a $C_1$ to $C_{18}$ hydrocarbon group that may optionally be substituted with a —$NH_2$ or —COOH and $R_2$ is defined above is also cleared more slowly from dogs than fluorfenicol. Accordingly, the invention further relates to a method of treating a bacterial infection in a dog comprising administering to a dog in need thereof a Fenicol Compound of formula (V). In one embodiment, Z in the Fenicol Compound of formula (V) is hydrogen. In one embodiment Z in the Fenicol Compound of formula (V) is an acyl group of formula —C(O)—$R_2$, wherein $R_2$ is a $C_1$ to $C_{18}$ hydrocarbon group that may optionally be substituted with a —$NH_2$ or —COOH and $R_2$ is defined. In one embodiment, Z in the Fenicol Compound of formula (V) is an acyl group of formula —C(O)—$R_2$, wherein $R_2$ is a $C_1$ to $C_{18}$ hydrocarbon group that is unsubstituted. In one embodiment, Z in the Fenicol Compound of formula (V) is an acetyl group. In one embodiment, Z in the Fenicol Compound of formula (V) is a butanoyl group. In one embodiment, Z in the Fenicol Compound of formula (V) is a hexanoyl group.

It has also unexpectedly been discovered that the clearance rate of Fenicol compounds wherein the acylamido group is in the (R) stereochemical configuration differs from the clearance rate of Fenicol Compounds wherein the acylamido group is in the (S) stereochemical configuration. Typically, the Fenicol Compound wherein the acylamido group is in the (R) stereochemical configuration has a slower clearance rate. Accordingly, administering a Fenicol Compound wherein the acylamido group is present as a single stereochemical configuration substantially free of the other stereochemical configuration, preferably the (R) stereochemical configuration substantially free of the (S) stereochemical configuration, can provide higher serum concentrations of the Fenicol Compound, a better therapeutic profile, and a more effective treatment for bacterial infections than administering a Fenicol Compound wherein the acylamido group is an equimolar mixture of the (R) stereochemical configuration and the (S) stereochemical configuration.

FIG. 3 depicts the serum concentration of Fenicol Compound A2 wherein the acylamido group is present in the (R) stereochemical configuration and the serum concentration of Fenicol Compound A2 wherein the acylamido group is present in the (S) stereochemical configuration as a function of time when Fenicol Compound A2 wherein the acylamido group is present as an equimolar mixture of the (R) stereochemical configuration and the (S) stereochemical configuration was administered to dogs subcutaneously at a dose of 40 mg/kg as a formulation containing 925 g of Fenicol Compound A2 wherein the acylamido group is present as an equimolar mixture of the (R) stereochemical configuration and the (S) stereochemical configuration, 2 mL N-methylpyrrolidone, 0.5 mL propylene glycol, QS to 5 mL with polyethylene glycol. Serum concentrations of Fenicol Compound A2 wherein the acylamido group is present in the (R) stereochemical configuration and Fenicol Compound A2 wherein the acylamido group is present in the (S) stereochemical configuration were measured as a function of time using high pressure liquid chromatography ("HPLC") and the maximum serum level was determined for each isomer ($C_{maxR}$, and $C_{maxS}$, respectively). The percent of the Fenicol compound wherein the acylamido group has the (R) stereochemical configuration was then determined at each time point by dividing the serum concentration of Fenicol compound wherein acylamido group has the (R) stereochemical configuration by $C_{maxR}$. Similarly, the percent of the Fenicol Compound wherein the acylamido group has the (S) stereochemical configuration was determined at each time point by dividing the serum concentration of Fenicol Compound wherein the acylamido group has the (S) stereochemical configuration by $C_{maxS}$. FIG. 3 graphically depicts the percent of the Fenicol Compound wherein the acylamido group has the (R) stereochemical configuration and the percent of Fenicol Compound wherein the acylamido group has the (S) stereochemical configuration as a function of time. FIG. 3 shows that Fenicol Compound A2 wherein the acylamido group has the (R) stereochemical configuration is cleared more slowly than Fenicol Compound A2 wherein the acylamido group has the (S) stereochemical configuration.

Accordingly, the invention further relates to a method of treating a bacterial infection in an animal comprising administering to an animal in need thereof a compound of formula (III):

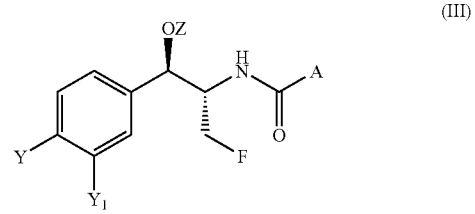

or a pharmaceutically acceptable salt thereof, wherein A is a group of formula —CH($CH_3$)($CF_3$), —CH($CH_3$)(halo), —CH($CF_3$)(halo), —CH($CF_3$)(OH);

Z is hydrogen or an acyl group of formula —C(O)—$R_2$, wherein $R_2$ is a $C_1$ to $C_{18}$ hydrocarbon group that may optionally be substituted with a —$NH_2$ or —COOH;

Y and $Y^1$ is —H; —$NO_2$; —$SO_2R_1$; —$SOR_1$—$SR_1$; —$SONH_2$; —$SO_2NH_2$; —$SONHR_1$; —$SO_2NHR_1$; —$COR_2$; —$OR_1$; —$R_1$; —CN, -halogen; -phenyl; or -phenyl substituted with -halogen, —$NO_2$, —$SO_2CH_3$, —$R_1$, or —$OR_1$;

halo is —Cl, —Br, —I, or —F; and $R_1$ is a $C_1$ to $C_3$ hydrocarbon group;

wherein the group of formula A is in either the (R) configuration substantially free of the (S) configuration or the (S) configuration substantially free of the (R) configuration and the configuration of the group of formula A is the configuration that provides the compound of formula (III) that is cleared more slowly when administered to an animal.

The invention further relates to a method of selecting a compound for treating a condition in an animal comprising:

(i) providing a first compound that has a first carbon atom that is achiral and bonded to four first substituents;

(ii) modifying the first compound that has a first carbon atom that is achiral by replacing a sufficient number of the first substituents with second substituents to provide a second compound wherein the first carbon atom has been changed to a chiral carbon atom, and wherein the second compound exists as a mixture of the second compound wherein the chiral carbon atom has the R stereochemical configuration and the second compound wherein the chiral carbon has the S stereochemical configuration;

(iii) separating the second carbon compound wherein the chiral carbon atom has the R stereochemical configuration and the second carbon compound wherein the chiral carbon atom has the S stereochemical configuration;

(iv) testing the second carbon compound that has the chiral carbon in the R stereochemical configuration and the second carbon compound that has the chiral carbon atom bonded in the S stereochemical configuration for activity at treating the condition;

(v) selecting the second carbon compound that has the higher activity for treating the condition.

In one embodiment, the condition is a bacterial infection.

In one embodiment, the second carbon compound that has the higher activity for treating the condition is selected based on its rate of clearance in the animal.

In one embodiment, the rate of clearance in the animal of the second carbon compound that has the higher activity for treating the condition is the second carbon compound that is cleared more slowly.

The invention further relates to a chemical compound selected using the method of selecting a compound for treating a condition in an animal.

5.8 Therapeutic/Prophylactic Administration and Compositions of the Invention

5.8.1 Theraputic/Prophylactic Administration

Due to their activity, the Fenicol Compounds are advantageously useful in veterinary and human medicine. As described above, the Fenicol Compounds are useful for treating or preventing a bacterial infection in an animal in need thereof.

When administered to an animal, the Fenicol Compounds are administered as a component of a composition that comprises a pharmaceutically acceptable carrier or excipient. The Fenicol Compounds of the invention can be administered by any convenient route, for example, orally, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, tablets, etc., and can be used to administer the Fenicol Compounds.

Methods of administration include, but are not limited to, intradermal; intramuscular; intraperitoneal; intravenous; subcutaneous; intranasal; epidural; oral; sublingual; intracerebral; intravaginal; transdermal; rectal; by inhalation; or topical, particularly to the ears, nose, eyes, or skin. The mode of administration is left to the discretion of the practitioner. In most instances, administration will result in the release of the Fenicol Compound into the bloodstream.

In one embodiment, the Fenicol Compound is administered orally.

In one embodiment, the Fenicol Compound is administered as a subcutaneous injection.

In one embodiment, the Fenicol Compound is administered as an intramuscular injection.

In one embodiment, the Fenicol Compound is administered intravenously.

In one embodiment, the Fenicol Compounds are delivered topically.

In one embodiment, the Fenicol Compounds are adminsitered by simply mixing the Fenicol Compound with the animal's feed.

In yet another embodiment, the Fenicol Compounds can be delivered in a controlled-release system or sustained-release system (see, e.g., Goodson, in Medical Applications of Controlled Release, supra, vol. 2, pp. 115-138 (1984)). Controlled- or sustained-release systems such as those discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of the Fenicol Compounds, thus requiring only a fraction of the systemic dose.

In specific embodiments, it can be desirable to administer the Fenicol Compounds locally. This can be achieved, for example, and not by way of limitation, by local infusion during surgery, topical application, e.g., in conjunction with a wound dressing after surgery, by injection, or by means of an implant, said implant being of a porous, non-porous, or gelatinous material, including membranes, such as sialastic membranes or fibers.

The amount of the Fenicol Compound that is effective in the treatment or prevention of a bacterial infection can be determined by standard clinical techniques. In addition, in vitro or in vivo assays can optionally be employed to help identify optimal dosage ranges. The precise dose to be employed will also depend on the route of administration, the seriousness or severity of the bacterial infection, the susceptibility of the infecting organism to the Fenicol Compound, and the characteristics of the animal being treated and can be decided according to the judgment of a practitioner and/or each animal's circumstances. Suitable effective dosage amounts, however, typically range from about 0.1 mg/kg of body weight to about 50 mg/kg of body weight, preferably about 0.5 mg/kg of body weight to about 25 mg/kg of body weight, more preferably 0.75 mg/kg of body weight to about 20 mg/kg of body weight, and most preferably 1 mg/kg of body weight to about 15 mg/kg of body weight. The effective dosage amounts described herein refer to total amounts administered; that is, if more than one Fenicol Compound is administered, the effective dosage amounts correspond to the total amount administered.

In one embodiment, an effective dosage amount is administered about every 7 days until the bacterial infection is abated.

In one embodiment, an effective dosage amount is administered about every 7 days for 4 weeks.

In one embodiment, an effective dosage amount is administered about every 7 days for 2 weeks.

In one embodiment, a single effective dosage amount is administered.

In one embodiment, 2 effective dosage amount are administered 24 hours apart.

In one embodiment, 2 effective dosage amount are administered 48 hours apart.

In one embodiment, an effective dosage amount is administered about every 24 h until the bacterial infection is abated.

In one embodiment, an effective dosage amount is administered about every 12 h until the bacterial infection is abated.

In one embodiment, an effective dosage amount is administered about every 24 h for about 4 weeks.

In one embodiment, an effective dosage amount is administered about every 12 h for about 4 weeks.

In one embodiment, an effective dosage amount is administered about every 24 h for about 2 weeks.

In one embodiment, an effective dosage amount is administered about every 12 h for about 2 weeks.

In one embodiment, an effective dosage amount is administered about every 24 h for about 1 week.

In one embodiment, an effective dosage amount is administered about every 12 h for about 1 week.

In one embodiment, an effective dosage amount is administered daily until the bacterial infection is abated. The daily dose may be divided into about 2 to 4 individual doses.

Typically, topical compositions are applied from about 1 to 5 times each day until the bacterial infection is abated. In one embodiment, the topical compositions are applied once each day. In one embodiment, the topical compositions are applied twice each day. In one embodiment, the topical compositions are applied three times each day. In one embodiment, the topical compositions are applied four times each day. In one embodiment, the topical applications are applied for 4 weeks. In one embodiment, the topical applications are applied for 3 weeks. In one embodiment, the topical applications are applied for 2 weeks. In one embodiment, the topical applications are applied for 1 week.

The present methods for treating or preventing a bacterial infection in an animal in need thereof can further comprise administering another therapeutic agent to the animal being administered a Fenicol Compound. In one embodiment, the other therapeutic agent is administered in an effective amount.

The other therapeutic agent include, but are not limited to, other antibiotics, antifungal agents, antiviral agents, antiparasitic agents, and anti-inflammatory agents.

Examples of useful antibiotics include, but are not limited to, amoxicillin; ampicillin; ceftiofor; erythromycin; oxytetracycline; procaine penicillin G; sulfonamides; tylosin; tilmicosin; cephalosporins; chloramphenicol; aminoglycosides such as kanamycin and gentamycin; metronidazole; clindamycin; and tetracycline (See, e.g., Bradford P. Smith, *Large Animal Internal Medicine*, 2$^{nd}$ ed. Mosby, St. Louis, 1996 p. 644 and S. Birchard and R. Sherding, *Saunders Manual of Small Animal Practice*, W. B. Saunders Company, Philadelphia, 1994 p. 739).

Examples of useful antifungal agents include, but are not limited to amphotericin B, ketaconazole, miconazole, 5-fluorocytosine, enilconazole, itraconazole, thiabendazole, and iodides (See, e.g., Bradford P. Smith, *Large Animal Internal Medicine*, 2$^{nd}$ ed. Mosby, St. Louis, 1996 p. 576 and S. Birchard and R. Sherding, *Saunders Manual of Small Animal Practice*, W. B. Saunders Company, Philadelphia, 1994 p. 576).

Examples of useful antiviral agents include, but are not limited to, interferon (See; e.g., Bradford P. Smith, *Large Animal Internal Medicine*, 2$^{nd}$ ed. Mosby, St. Louis, 1996 p. 646).

Examples of useful antiparasitic agents include, but are not limited to, benzimidazoles, such as thiabendazole, fenbendazole, mebendazole, oxfendazole, oxibendazole, albendazole, parbendazole, and febantel; tetrahydropyridines such as morantel tartrate/pyrantel pamoate; levamisole, organophosphates such as haloxon, coumaphos, trichlorfon, and dichlorvos; piperazine salts; ivermectin; and phenothiazine (See, e.g., Bradford P. Smith, *Large Animal Internal Medicine*, 2$^{nd}$ ed. Mosby, St. Louis, 1996 p. 1688).

Examples of useful antiinflammatory agents include, but are not limited to, corticosteroids such as dexamethasone; antihistamines, and non-steroidal antiinflammatory drugs such as aspirin, flunixin meglumine, phenylbutazone, and ibuprofin (See, e.g., Bradford P. Smith, *Large Animal Internal Medicine*, 2$^{nd}$ ed. Mosby, St. Louis, 1996 p. 645).

Effective amounts of the other therapeutic agents are known to those skilled in the art. It is well within the skilled artisan's purview to determine the other therapeutic agent's optimal effective-amount range. In one embodiment of the invention, where another therapeutic agent is administered to an animal, the effective amount of the Fenicol Compound is less than its effective amount would be were the other therapeutic agent not administered. In this case, without being bound by theory, it is believed that the Fenicol Compound and the other therapeutic agent act synergistically to treat or prevent a bacterial infection.

The Fenicol Compound and the other therapeutic agent can act additively or, in one embodiment, synergistically. In one embodiment, a Fenicol Compound is administered concurrently with another therapeutic agent; for example, a composition comprising an effective amount of a Fenicol Compound and an effective amount of another therapeutic agent can be administered. Alternatively, a composition comprising an effective amount of a Fenicol Compound and a different composition comprising an effective amount of another therapeutic agent can be concurrently administered. In another embodiment, an effective amount of a Fenicol Compound is administered prior or subsequent to administration of an effective amount of another therapeutic agent. In this embodiment, the Fenicol Compound is administered while the other therapeutic agent exerts its therapeutic effect, or the other therapeutic agent is administered while the Fenicol Compound exerts its therapeutic effect for treating or preventing a bacterial infection.

In one embodiment, a mixture of two Fenicol Compounds of the invention are administered simultaneously. For example, a composition comprising both a Fenicol Compound wherein the acylamido group of Fenicol Compound is in both the (R) stereochemical configuration and a Fenicol Compound wherein the acylamido group of Fenicol Compound is in the (S) stereochemical configuration is administered to an animal. In one embodiment, the ratio of the Fenicol Compound with the acylamido groups in the (R) stereochemical configuration and the Fenicol Compound with the acylamido groups of Fenicol Compounds (S) stereochemical configuration is not 1:1. Administering such compositions to an animal allows the serum concentration of total Fenicol Compounds as a function of time to be controlled.

FIG. 3 shows that Fenicol Compound A2 wherein the acylamido group is present in the (S) stereochemical configuration, when administered to dogs, provides a rapid increase in the serum concentration of Fenicol Compound A2 that then decreases rapidly. In contrast, Fenicol Compound A2 wherein the acylamido group is present in the (R) stereochemical configuration, when administered to dogs, provides a rapid increase in the serum concentration of Fenicol Compound A2 that then decreases much more slowly than Fenicol Compound A2 wherein the acylamido group is in the (S) stereochemical configuration. Accordingly, by varying the ratio of Fenicol Compound A2 wherein the acylamido groups is in the (R) stereochemical configuration to Fenicol Compound A2 wherein the acylamido group is in the (S) stereochemical configuration in a pharmaceutical composition it is possible to control the serum concentration of the Fenicol Compound so as to maximize the therapeutic effect. For example, a pharmaceutical composition having Fenicol Compound A2 wherein the acylamido group is in the (S) stereochemical configuration will provide a serum level of Fenicol Compound that increases and then rapidly decreases. In contrast, a pharmaceutical composition having Fenicol Compound A2 wherein the acylamido group is in the (R) stereochemical configuration will provide a serum level of Fenicol Compound that increases and then decreases more slowly.

5.8.2 Pharmaceutical Compositions Comprising Fenicol Compounds

Compositions comprising a Fenicol Compound can take the form of solutions, suspensions, emulsions, tablets, pills, pellets, capsules, capsules containing liquids, powders, sustained-release formulations, suppositories, aerosols, sprays, suspensions, or any other form suitable for use. In one embodiment, the composition is in the form of a tablet or capsule (See e.g., U.S. Pat. No. 5,698,155).

In one embodiment, the Fenicol Compounds are formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Tablet and pill form are the preferred form for oral delivery. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions are preferred for bacterial infections of the gastrointestinal tract that can cause diarrhea.

In one embodiment, the Fenicol Compounds are formulated for subcutaneous injection, intramuscular injection, or intravenous administration. Typically, compositions for subcutaneous injection, intramuscular injection, or intravenous administration comprise sterile isotonic aqueous buffer. Where necessary, the compositions can also include a solubilizing agent. Non-aqueous compositions can also be used. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the Fenicol Compounds are to be administered by infusion, they can be dispensed, for example, with an infusion bottle containing sterile pharmaceutical grade water or saline. Where the Fenicol Compounds are administered by injection, an ampule of sterile water for injection or saline can be provided so that the ingredients can be mixed prior to administration.

Compositions for oral, subcutaneous injection, intramuscular injection, or intravenous administration typically contain the Fenicol Compound in an amount ranging from about 1 percent to 80 percent by weight of the pharmaceutical compositions. In one embodiment, the compositions contain the Fenicol Compound in an amount ranging from about 5 percent to 75 percent by weight of the pharmaceutical compositions. In one embodiment, the compositions contain the Fenicol Compound in an amount ranging from about 10 percent to 70 percent by weight of the pharmaceutical compositions. In one embodiment, the compositions contain the Fenicol Compound in an amount ranging from about 15 percent to 65 percent by weight of the pharmaceutical compositions. In one embodiment, the compositions contain the Fenicol Compound in an amount ranging from about 20 percent to 55 percent by weight of the pharmaceutical compositions.

In another embodiment, the Fenicol Compounds are formulated for topical administration. Compositions for topical administration can be in the form of a salve, gel, lotion, cream, or ointment. Compositions for topical administration can be either hydrophillic or hydrophobic and can be aqueous or non-aqueous. Compositions for topical administration can be in the form of an emulsion.

For topical administration, the compositions typically contain the Fenicol Compound in an amount ranging from about 0.05 to 10 weight percent of the topical formulation, preferably about 0.05 to 5 weight percent of the topical formulation, more preferably about 0.07 to 4 weight percent of the topical formulation, and most preferably about 0.1 to 3 weight percent of the topical formulation.

The present compositions can optionally comprise a suitable amount of a pharmaceutically acceptable excipient so as to provide the form for proper administration to the animal. Such pharmaceutical excipients can be liquids, such as water and oils, including those of petroleum, animal, vegetable, or synthetic origin, such as peanut oil, soybean oil, mineral oil, sesame oil, and the like. Pharmaceutically acceptable excipients include, but are not limited to, binding agents, filling agents, lubricating agents, suspending agents, sweeteners, flavoring agents, preservatives, buffers, wetting agents, disintegrants, effervescent agents, coloring agents, pH buffering agents, and other excipients depending upon the route of administration and the dosage form desired. Such excipients are known in the art. Examples of suitable pharmaceutical excipients are described in *Remington's Pharmaceutical Sciences* 1447-1676 (Alfonso R. Gennaro ed., 19th ed. 1995), the contents of which are incorporated herein by reference.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH 102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as fructose, sucrose, xylitol, sodium saccharin, cyclamate, aspartame, and acsulfame. Examples of flavoring agents are Magnasweet® (trademark of MAFCO); oil of wintergreen; bubble gum flavor; peppermint flavor; spearmint flavor; fruit flavors such as cherry, grape, and orange; and the like. Sweetners and flavoring agents are particularly useful in orally administered dosage forms to provide a pharmaceutically palatable preparation.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In one embodiment, the pharmaceutically acceptable excipients are sterile when administered to an animal. Water, and in one embodiment physiological saline, is a particularly useful excipient when the Fenicol Compound is administered intravenously. Saline solutions and aqueous dextrose and glycerol solutions can also be employed as liquid excipients, particularly for injectable solutions. In one embodiment, the liquid excipient is a non-aqueous solvent such as N-methyl-2-pyrollidone; a mixture of N-methyl-2-pyrollidone, polyethylene glycol, and propylene glycol; or the solvents described in U.S. Pat. No. 5,082,863 to Apelian, the contents of which are expressly incorporated herein by reference.

The composition of the invention are prepared by a method comprising admixing a Fenicol Compound and a pharmaceutically acceptable carrier or excipient. Admixing can be accomplished using methods well known for admixing a compound and a pharmaceutically acceptable carrier or excipient.

5.9 Kits

The invention encompasses kits that can simplify the administration of a Fenicol Compound to an animal. A typical kit of the invention comprises a unit dosage form of a Fenicol Compound. In one embodiment, the unit dosage form is a container, which can be sterile, containing an effective amount of a Fenicol Compound and a pharmaceutically acceptable carrier or excipient. The kit can further comprise a label or printed instructions instructing the use of the Fenicol Compound to treat a bacterial infection. The kit can also further comprise a unit dosage form of another therapeutic agent, for example, a second container containing an effective amount of the other therapeutic agent and a pharmaceutically acceptable carrier or excipient. In another embodiment, the kit comprises a container containing an effective amount of a Fenicol Compound, an effective amount of another therapeutic agent and a pharmaceutically acceptable carrier or excipient. Examples of other therapeutic agents include, but are not limited to, those listed above.

Kits of the invention can further comprise a device that is useful for administering the unit dosage forms. Examples of such a devices include, but are not limited to, a syringe, a drip bag, a dropper, and a patch.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

6. EXAMPLES

Examples 1 to 7 relate to the synthesis of illustrative Fenicol Compounds of the invention.

6.1 Synthesis of Fenicol Compound A1

To a suspension of D-(threo)-1-p-methylsulfonyl-2-amino-3-fluoro-1-propanol (0.111 g, 0.45 mmol, 1 eq.) in 2.5 mL of DCM was added isobutyric anhydride with stirring to provide a thick mixture. After 5 min., 1.5 mL of DCM was added to the thick mixture and the resulting solution was allowed to stir for 30 min. An additional 25 mL of DCM was then added to the mixture and the resulting DCM mixture extracted with water (20 mL) followed by 5% NaHCO$_3$ (20 mL). The organic extract was dried (Na$_2$SO$_4$) and the solvent removed under reduced pressure to provide Fenicol Compound A1 that can be purified using silica gel column chromatography eluted with 70% ethyl acetate in hexane.

6.2 Synthesis of Fenicol Compound A2

To a solution of D-(threo)-1-p-methylsulfonyl-2-amino-3-fluoro-1-propanol (2.89 g, 11.69 mmol, 1 eq.) in 50 mL of DCM was added 3,3,3-trifluoro-2-methyl propionic acid (1 eq.) followed by an additional 50 mL of DCM. To the resulting solution was then added EDC (1 eq.) and HOBT (1 eq.) with stirring. The resulting mixture was allowed to stir for about 12 h. and was then washed with water (2×100 mL), dried (Na$_2$SO$_4$), and the solvent removed under reduced pressure to provide Fenicol Compound A2 that can be purified using silica gel column chromatography eluted with 5% methanol in chloroform.

6.3 Synthesis of Fenicol Compound I2

To a solution of (S)-2-chloropropionic acid (5 g, 46.08 mmol, 1 eq.) and N-hydroxysuccinimide (1 eq.) in THF (50 mL) at about 0° C. was added a solution of dicyclohexylcarbodiimide (1 eq.) in 20 mL of THF at about 0° C. and the resulting solution allowed to stir for about 2 h. at about 0° C. and then maintained at about 4° C. for about 12 h to provide a solution of the N-hydroxysuccinimide ester of (S)-2-chloropropionic acid.

Separately a solution of D-(threo)-1-p-methylsulfonyl-2-amino-3-fluoro-1-propanol (7.4 g, 30 mmol) in 150 mL of THF was added dropwise the 70 mL solution of the N-hydroxysuccinimide ester of (S)-2-chloropropionic acid (1.5 eq.) prepared above at 0° C. and the resulting solution allowed to stir for about 3 h. The resulting solution was then quenched with water, the THF removed under reduced pressure, and the resulting aqueous mixture extracted with DCM (150 mL). The DCM solution was dried ($Na_2SO_4$), and the solvent removed under reduced pressure to provide Fenicol Compound I2 that can be purified by recrystallization from ethanol.

6.4 Synthesis of Fenicol Compound A7

To a solution of D-(threo)-1-p-methylsulfonyl-2-amino-3-fluoro-1-propanol (0.5 g, 2.0 mmol, 1 eq.) in DMF (6 mL) was added 2,3,3,3-tetrafluoropropionic acid (1.2 eq.) followed by BOP (1.2. eq.) and HOBT (1.2 eq.) and the resulting solution was allowed to stir for about 48 h. DCM (150 mL) was added to the solution and the resulting solution extracted with 5% $NaHCO_3$, brine, and water; dried ($Na_2SO_4$); and the solvent removed under reduced pressure to provide Fenicol Compound A7 that can be purified by recrystallization.

6.5 Synthesis of Fenicol Compound I9

To a solution of D-(threo)-1-p-methylsulfonyl-2-amino-3-fluoro-1-propanol (0.5 g, 2.0 mmol, 1 eq.) in DMF (5 mL) was added (S)-3,3,3-trifluoro-2-hydroxy propionic acid (1.2 eq.) followed by EDC (1.2. eq.) and HOBT (1.2 eq.) and the resulting solution allowed to stir for about 40 h. DCM (150 mL) was added to the solution and the resulting solution extracted with 5% $NaHCO_3$, brine, and water; dried ($Na_2SO_4$); and the solvent removed under reduced pressure to provide Fenicol Compound I9 that can be purified by recrystallization from ethanol.

6.6 Synthesis of Fenicol Compound E2

To a solution of (R)-2-chloropropionic acid (16.3 g, 150 mmol, 1 eq.) and N-hydroxysuccinimide (1 eq.) in THF (150 mL) at about 0° C. was added a solution of DCC (1 eq.) in 50 mL of THF at about 0° C. and the resulting solution allowed to stir for about 30 min. at about 0° C. and then maintained at about 4° C. for about 12 h to provide a solution of the N-hydroxysuccinimide ester of (R)-2-chloropropionic acid.

Separately a solution of D-(threo)-1-p-methylsulfonyl-2-amino-3-fluoro-1-propanol (7.4 g, 30 mmol) in 150 mL of THF was added dropwise to the 60 mL of a solution of the N-hydroxysuccinimide ester of (R)-2-chloropropionic acid (1.5 eq.) prepared above at 0° C. and the resulting solution allowed to stir for about 3 hr. The resulting solution was then quenched with water, the THF removed under reduced pressure, and the resulting aqueous mixture extracted with DCM (150 mL). The DCM solution was dried ($Na_2SO_4$), and the solvent removed under reduced pressure to provide Fenicol Compound E2 that can be purified by recrystallization from ethanol.

6.7 Administration of of Fenicol Compound A1 to Dogs

Fenicol Compound A1 was formulated as a pharmaceutical composition containing 150 mg of Fenicol Compound A1, 25 mL N-methylpyrrolidone, 25 mL propylene glycol, QS to 100 mL with polyethylene glycol. The pharmaceutical composition was then administered to dogs at a dose of 40 mg/kg. Blood samples were taken from the dog at various time points and serum separated using standard methods well known to those skilled in the art. The serum was then analyzed using HPLC according to the following procedure:

A $C_{18}$ Sep-Pak Plus® cartridge (Sep-Pak) (commercially available from Waters of Milford, Mass.) was rinsed with 5 mL of methanol followed by 5 mL of water and loaded with 1 mL of serum. After loading, the Sep-Pak was washed with 2 mL of water, 2 mL of 15% aqueous acetonitrile, and 3 mL of hexane. The Sep-Pak was then eluted with 4 mL of acetonitrile and the eluant collected. The acetonitrile was evaporated using a stream of nitrogen to provide a residue and the resulting residue was reconstituted with 1 mL of 25% aqueous acetonitrile to provide an assay solution. 50 µL of the assay solution was then analyzed by HPCL using high pressure liquid chromatography equipped with a Beckman Coulter Ultraphere C-18 5 µM×4.6 mm×250 mm analytical column eluted at a flow of 1.2 mL/min. using a gradient of water and acetonitrile according to the following profile:

| Time (min.) | Percent Water | Percent Acetonitrile |
| --- | --- | --- |
| 0 | 75 | 25 |
| 4 | 75 | 25 |
| 10 | 40 | 60 |
| 20 | 40 | 60 |
| 25 | 75 | 25 |
| 42 | 75 | 25 |

The HPLC system was interfaced to a UV detector operated at 223 nm. The serum concentration of Fenicol Compound A1 was then determined by comparing the area under the curve for the HPLC peak corresponding to Fenicol Compound A1 to a standard curve of peak areas v. known concentrations of Fenicol Compound A1 in cat serum. The standard curve was prepared using the following concentrations of Fenicol Compound A1 in cat serum 0.1, 0.3, 1, 2, 3, 5, 7, and 10 µg/mL.

FIG. 1 is a plot of the serum concentration of Fenicol Compound A1 as a function of time following subcutaneous administration of Fenicol Compound A1 to dogs at a dose of 40 mg/kg as a pharmaceutical composition containing 3 g of Fenicol Compound A1, 9 g N-methyl pyrrolidone, 2.25 g propylene glycol, QS to 20 mL with polyethylene glycol. FIG. 1 also shows the serum concentration when NUFLOR® (commercially available from Schering-Plough Animal Health, New Jersey) was administered to dogs at a dose of 40 mg/kg. FIG. 1 shows that Fenicol Compound A1, when administered to dogs, acheives a higher serum concentration than NUFLOR® and is cleared more slowly than NUFLOR®. Therefore administering Fenicol Compound A1 to dogs results in a higher serum concentration of the antibiotic than is obtainable when NUFLOR® is administered to dogs. Accordingly, Fenicol Compound A1 can be more effective than NUFLOR® at treating or preventing a bacterial infection in dogs and other small animals.

6.8 Administration of Fenicol Compound A2 to Dogs

Fenicol Compound A2 was formulated as a pharmaceutical composition containing 925 mg of Fenicol Compound A2, 2 mL N-methylpyrrolidone, 0.5 mL propylene glycol, QS to 5 mL with polyethylene glycol. The pharmaceutical composition was then administered to dogs subcutaneously at a a dose of 40 mg/kg. Blood samples were taken from the dogs at various time points and the blood samples treated as described above. The serum was then analyzed using the HPLC procedure described above.

FIG. 2 is a plot of the serum concentration of Fenicol Compound A2 as a function of time following the subcutaneous administration. FIG. 2 shows that Fenicol Compound A2, when administered to dogs, achieves a much higher serum concentration and is cleared more slowly than is NUFLOR®. Therefore, administering Fenicol Compound A2 to dogs results in a higher serum concentration of the antibiotic than is obtainable when NUFLOR® is administered to dogs. Accordingly, Fenicol Compound A2 can be more effective than NUFLOR® at treating or preventing a bacterial infection in dogs and other small animals.

6.9 Administration of Fenicol Compound A2 to Dogs

Fenicol Compound A2, i.e., wherein the acylamido group is present as an equimolar mixture of the (R) stereochemical configuration and the (S) stereochemical configuration, was formulated as a pharmaceutical composition containing 925 mg of Fenicol Compound A2, 2 mL N-methylpyrrolidone, 0.5 mL propylene glycol, QS to 5 mL with polyethylene glycol. The pharmaceutical composition was then administered to dogs subcutaneously at a a dose of 40 mg/kg. Blood samples were taken from the dogs at various time points and the blood samples treated as described above. The serum was then analyzed using the HPLC procedure described above. The HPLC method is capable of separating Fenicol Compound A2 wherein the acylamido group is in the (R) configuration (i.e., Fenicol Compound I1) and Fenicol Compound A2 wherein the acylamido group is in the (S) configuration (i.e., Fenicol Compound E1). The maximum serum level was determined for each isomer ($C_{maxR}$ and $C_{maxS}$, respectively). The percent of Fenicol Compound A2 wherein the acylamido group has the (R) stereochemical configuration was then determined at each time point by dividing the serum concentration of the Fenicol Compound A2 wherein the acylamido group has the (R) stereochemical configuration at that time point by $C_{maxR}$. Similarly, the percent of Fenicol Compound A2 wherein the acylamido group has the (S) stereochemical configuration was then determined at each time point by dividing the serum concentration of the Fenicol Compound A2 wherein the acylamido group has the (S) stereochemical configuration at that time point by $C_{maxS}$.

FIG. 3 graphically depicts the percent of Fenicol Compound A2 wherein the acylamido group has the (R) stereochemical configuration and the percent of Fenicol Compound A2 wherein the acylamido group has the (S) stereochemical configuration as a function of time. FIG. 3 shows that Fenicol Compound A2 wherein the acylamido group has the (R) stereochemical configuration is cleared more slowly than Fenicol Compound A2 wherein the acylamido group has the (S) stereochemical configuration.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference.

What is claimed is:

1. A compound of formula (III):

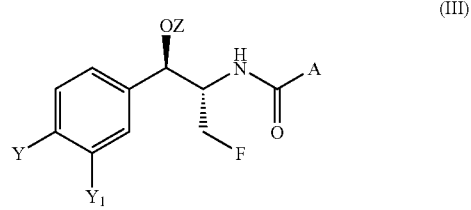

(III)

or a pharmaceutically acceptable salt thereof,
wherein
A is (R) —CH(CH$_3$)(CF$_3$) substantially free of (S) —CH(CH$_3$)(CF$_3$), (R) —CH(CF$_3$)(halo) substantially free of (S) —CH(CF$_3$)(halo), or (R)-CH(CF$_3$)(OH) substantially free of (S) —CH(CF$_3$)(OH),
Z is hydrogen;
Y is —SO$_2$CH$_3$,
Y$_1$ is hydrogen, and
halo is —Cl, —Br, —I, or —F.

2. The compound of claim 1, wherein A is (R) —CH(CH$_3$)(CF$_3$) substantially free of (S) —CH(CH$_3$)(CF$_3$).

3. The compound of claim 1, wherein A is (R) —CH(CF$_3$)(halo) substantially free of (S) —CH(CF$_3$)(halo).

4. The compound of claim 3, wherein A is (R) —CH(CF$_3$)(Cl) substantially free of (S) —CH(CF$_3$)(Cl).

5. The compound of claim 3, wherein A is (R) —CH(CF$_3$)(F) substantially free of (S) —CH(CF$_3$)(F).

6. The compound of claim 3, wherein A is (R) —CH(CF$_3$)(Br) substantially free of (S) —CH(CF$_3$)(Br).

7. The compound of claim 3, wherein A is (R) —CH(CF$_3$)(I) substantially free of (S) —CH(CF$_3$)(I).

8. The compound of claim 1, wherein A is (R) —CH(CF$_3$)(OH) substantially free of (S) —CH(CF$_3$)(OH).

9. A method of treating a bacterial infection in an animal, comprising administering to an animal in need thereof a compound of formula (III):

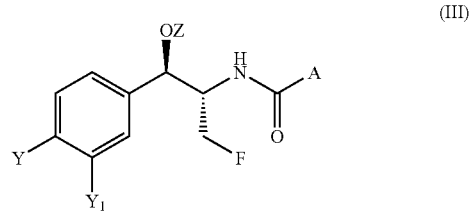

(III)

or a pharmaceutically acceptable salt thereof,
wherein
A is (R) —CH(CH$_3$)(CF$_3$) substantially free of (S) —CH(CH$_3$)(CF$_3$), (R) —CH(CH$_3$)(halo) substantially free of (S) —CH(CH$_3$)(halo), (R) —CH(CF$_3$)(halo) substantially free of (S) —CH(CF$_3$)(halo), (R)-CH(CF$_3$)(OH) substantially free of (S) —CH(CF$_3$)(OH), (5) —CH(CH$_3$)(CF$_3$) substantially free of (R) —CH(CH$_3$)(CF$_3$), (S) —CH(CH$_3$)(halo) substantially free of (R) —CH(CH$_3$)(halo), (S) —CH(CF$_3$)(halo) substantially free of (R) —CH(CF$_3$)(halo), or (S)-CH(CF$_3$) (OH) substantially free of (R) —CH(CF$_3$)(OH);

Z is hydrogen or an acyl group of formula —C(O)—R$_2$, wherein R$_2$ is a C$_1$ to C$_{18}$ hydrocarbon group that may optionally be substituted with a —NH2 or —COOH;

Y and Y$_1$ is —H; —NO2; —SO$_2$R$_1$; —SOR$_1$—SR$_1$; —SONH$_2$; —SO$_2$NH$_2$; —SONHR$_1$; —SO$_2$NHR$_1$; —COR$_2$; —OR; —R$_1$; —CN, -halogen; -phenyl; or -phenyl substituted with -halogen, —NO$_2$, —SO$_2$CH$_3$, —R$_1$, or —OR$_1$;

halo is —Cl, —Br, —I, or —F; and

R$_1$ is a C$_1$ to C$_3$ hydrocarbon group, wherein the bacterial infection is a bacterial infection caused by a bacteria that is susceptible to the compound of formula III.

10. The method of claim 9, wherein the animal is a dog or cat.

11. The method of claim 9, wherein the compound of formula (III) is administered at a dose ranging from about 0.1 mg/kg of body weight to about 50 mg/kg of body weight.

12. The method of claim 9, wherein the compound of formula (III) is administered daily until the bacterial infection is abated.

13. A method of treating a bacterial infection in an animal comprising administering to an animal in need thereof a compound of formula (III):

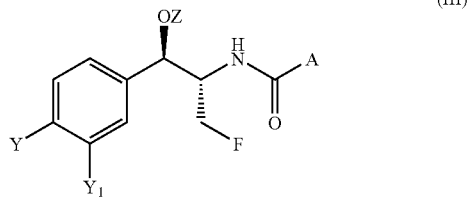

(III)

or a pharmaceutically acceptable salt thereof, wherein A is a group of formula —CH(CH$_3$)(CF$_3$), —CH(CH$_3$)(halo), —CH(CF$_3$)(halo), or —CH(CF$_3$)(OH);

Z is hydrogen or an acyl group of formula —C(O)—R$_2$, wherein R$_2$ is a C$_1$ to C$_{18}$ hydrocarbon group that may optionally be substituted with a —NH2 or —COOH;

Y and Y$_1$ is —H; —NO$_2$; —SO$_2$R$_1$; —SOR$_1$; —SR$_1$; —SONH$_2$; —SO$_2$NH$_2$; —SONHR$_1$; —SO2NHR$_1$; —COR$_2$; —OR; —R$_1$; —CN, -halogen; -phenyl; or -phenyl substituted with -halogen, —NO2, —SO$_2$CH$_3$, —R$_1$, or —OR$_1$;

halo is —Cl, —Br, —I, or —F; and

R$_1$ is a C$_1$ to C$_3$ hydrocarbon group; and wherein the group of formula A is in either the (R) configuration substantially free of the (S) configuration or the (S) configuration substantially free of the (R) configuration and is the configuration that is cleared more slowly when administered to an animal.

14. The method of claim 13, wherein Z is hydrogen.

15. The method of claim 13, wherein A is —CH(CH$_3$)(CF$_3$).

16. The method of claim 13, wherein A is —CH(CH$_3$)(halo).

17. The method of claim 13, wherein A is —CH(CF$_3$)(halo).

18. The method of claim 13, wherein A is or —CH(CF$_3$)(OH).

19. The method of claim 13, wherein A is —CH(CF$_3$)(Cl).

20. The method of claim 13, wherein A is —CH(CF$_3$)(Br).

21. The method of claim 13, wherein A is —CH(CF$_3$)(F).

22. The method of claim 13, wherein A is —CH(CF$_3$)(I).

23. The method of claim 13, wherein the compound of formula (III) is administered orally.

24. The method of claim 13, wherein the compound of formula (III) is administered by injection.

25. The method of claim 13, wherein the compound of formula (III) is administered topically.

* * * * *